US008859817B2

(12) United States Patent
Choi

(10) Patent No.: US 8,859,817 B2
(45) Date of Patent: Oct. 14, 2014

(54) PROCESS FOR PREPARATION OF PHENYL CARBAMATE DERIVATIVES

(75) Inventor: Yong Moon Choi, Fort Lee, NJ (US)

(73) Assignee: Bio-Pharm Solutions Co., Ltd. (KR)

( * ) Notice: Subject to any disclaimer, the term of this patent is extended or adjusted under 35 U.S.C. 154(b) by 89 days.

(21) Appl. No.: 13/338,863

(22) Filed: Dec. 28, 2011

(65) Prior Publication Data
US 2012/0184762 A1 Jul. 19, 2012

Related U.S. Application Data

(60) Provisional application No. 61/432,228, filed on Jan. 13, 2011.

(30) Foreign Application Priority Data

May 26, 2011 (KR) ........................ 10-2011-0049932

(51) Int. Cl.
C07C 213/06 (2006.01)
C07C 269/06 (2006.01)
C07C 45/45 (2006.01)
C07C 29/10 (2006.01)
C07C 29/48 (2006.01)
C07C 17/263 (2006.01)
C07F 7/18 (2006.01)
C07C 269/02 (2006.01)
C07C 41/48 (2006.01)

(52) U.S. Cl.
CPC .............. C07F 7/188 (2013.01); C07C 269/06 (2013.01); C07C 45/455 (2013.01); C07C 29/10 (2013.01); C07B 2200/07 (2013.01); C07C 29/48 (2013.01); C07C 17/263 (2013.01); C07F 7/1852 (2013.01); C07C 269/02 (2013.01); C07C 41/48 (2013.01)
USPC .......................................... 564/305; 564/306

(58) Field of Classification Search
USPC .................................. 556/443; 564/305, 306
See application file for complete search history.

(56) References Cited

U.S. PATENT DOCUMENTS

| 2,884,444 | A | 4/1959 | Berger et al. |
| 2,937,119 | A | 5/1960 | Berger et al. |
| 3,265,727 | A | 8/1966 | Bossinger et al. |
| 3,265,728 | A | 8/1966 | Bossinger et al. |
| 3,313,692 | A | 4/1967 | Bossinger et al. |
| 3,313,699 | A | 4/1967 | Bossinger et al. |
| 3,313,700 | A | 4/1967 | Bossinger et al. |
| 3,600,427 | A | 8/1971 | Verbiscar |
| 6,103,759 | A | 8/2000 | Choi et al. |
| 7,385,076 | B2 | 6/2008 | Patel et al. |
| 7,442,438 | B2 | 10/2008 | Boulos et al. |
| 7,737,141 | B2 | 6/2010 | Kimura et al. |
| 2001/0034365 | A1 | 10/2001 | Choi et al. |
| 2004/0138299 | A1 | 7/2004 | Cahill et al. |
| 2008/0103198 | A1 | 5/2008 | Haas |
| 2008/0317883 | A1 | 12/2008 | Choi et al. |
| 2009/0048213 | A1 | 2/2009 | Kimura et al. |
| 2009/0221640 | A1 | 9/2009 | Briggner et al. |
| 2013/0005801 | A1 | 1/2013 | Choi |
| 2014/0051753 | A9 | 2/2014 | Choi |

FOREIGN PATENT DOCUMENTS

| CN | 1208402 | A | 2/1999 |
| CN | 1536993 | A | 10/2004 |
| CN | 101208402 | A | 6/2008 |
| CN | 101472913 | A | 7/2009 |
| JP | 61-271992 | A | 12/1986 |
| WO | WO 2008/013213 | A1 | 1/2008 |
| WO | WO-2008/124848 | A1 | 10/2008 |
| WO | WO-2012/002773 | A2 | 1/2012 |
| WO | WO-2012/096458 | A2 | 7/2012 |

OTHER PUBLICATIONS

Citterio et al, J. Chem. Soc. Perkin Tran. I (1983), pp. 891-896.*
Ghosh et al, J. Org. Chem. (published 2010), pp. 500-511.*
Morimoto et al, J. Chem. Soc. Perkin Trans. II (1986), pp. 1205-1209.*
"European Application Serial No. 12169507.6, European Search Report mailed Sep. 26, 2012", 8 pgs.
Amarante, G. W., et al., "Acyloins from Morita-Baylis-Hillman adducts: an alternative approach to the racemic total synthesis of bupropion", Tetrahedron Letters, 49, (2008), 3744-3748.
Bausch, C. C., et al., "Cross Silyl Benzoin Additions Catalyzed by Lanthanum Tricyanide", J. Org. Chem., 69, (2004), 4283-4285.
Eid, Jr., C. N., et al., "Enantiomerically Pure Ketals in Synthesis, Diastereoselective Formation of β-Keto and β-Hydroxy Ketals", Tetrahedron Letters, 32(4), (1991),461-464.
Joseph, S. P., et al., "Reaction of chlorosulfonyl isocyanate with 1,2-diols", Synthetic Communications, 18(18), (1988), 2295-2302,
"International Application Serial No. PCT/KR2011/010105, International Search Report mailed Aug. 7, 2012", 3 pgs.
"U.S. Appl. No. 13/175,025, Non Final Office Action mailed Mar. 20, 2014", 9 pgs.
"U.S. Appl. No. 13/175,025, Final Office Action mailed Oct. 10, 2013", 10 pgs.
"U.S. Appl. No. 13/175,025, Non Final Office Action mailed May 16, 2013", 18 pgs.
"U.S. Appl. No. 13/175,025, Response filed Jan. 10, 2014 to Final Office Action mailed Oct. 10, 2013", 25 pgs.
"U.S. Appl. No. 13/175,025, Response filed Aug. 16, 2013 to Non Final Office Action mailed May 16, 2013", 28 pgs.
"U.S. Appl. No. 13/175,025, Supplemental Amendment filed Sep. 13, 2013", 7 pgs.
"International Application Serial No. PCT/KR2011/004862, International Search Report mailed Feb. 27, 2012", 3 pgs.
"International Application Serial No. PCT/KR2011/004862, Written Opinion mailed Feb. 27, 2012", 5 pgs.
"International Application Serial No. PCT/KR2011/010105. International Search Report mailed Aug. 7, 2012", 3 pgs.
"International Application Serial No. PCT/KR2011/010105, Written Opinion mailed Aug. 7, 2012", 4 pgs.

(Continued)

Primary Examiner — Kamal Saeed
Assistant Examiner — Janet L Coppins
(74) Attorney, Agent, or Firm — Schwegman Lundberg & Woessner, P.A.

(57) ABSTRACT

Provided are a process for the preparation of phenyl carbamate derivatives, useful in the treatment of CNS (central nervous system) disorders, an intermediate in the synthesis of the phenyl carbamate derivatives, and a process for preparation of the intermediate.

17 Claims, No Drawings

(56) References Cited

OTHER PUBLICATIONS

Girijavallabhan, V. M., et al., "Synthesis of the antifungal agent SCH 42427 (SM 9164)", *Bioorganic & Medicinal Chemistry Letters*, 1(7), 349-352, ASC on STN, Accession No. 1992:41371, (1991), 1 pg.

Jiao, P., et al., "A Sequential O-Nitrosoaldol and Grignard Addition Process: An Enantio-and Diastereoselective Entry to Chiral 1,2-Diols", *Angewandte Chemie, International Edition*, 48(18), (2009), 3333-3336.

U.S. Appl. No. 13/727,659, Non Final Office Action mailed Apr. 22, 2014, 6 pgs.

"Chinese Application Serial No. 2011 0063001.5, Office Action mailed Mar. 14, 2014", (w/ English Translation), 13 pgs.

"Japanese Application Serial No. 2013-518264, Office Action mailed Mar. 11, 2014", (w/English Translation), 6 pgs.

Edin, Michaela, et al., "Ruthenium- and lipase-catalyzed DYKAT of 1,2-diols: an enantioselective synthesis of syn-1,2-diacetates", *Tetrahedron: Asymmetry, 17(4)*, (2006), 708-715.

Girijavallabhan, V. M., "Synthesis of the Antifungal Agent Sch 42427 (SM 9164)", *Bioorganic & Medicinal Chemistry Letters*, 1(7), (1991), 349-352.

Ohta, Hiromichi, et al., "Reductive $C_2$-Homologation of Substituted Benzaldehydes by Fermenting Baker's Yeast", Agric. Biol. Chem. 50(5), (1986), 1261-1266.

\* cited by examiner

PROCESS FOR PREPARATION OF PHENYL CARBAMATE DERIVATIVES

CROSS-REFERENCE TO RELATED APPLICATION

This application claims priorities to and the benefits of U.S. Provisional Application No. 61/432,228 filed in the United States Patent and Trademark Office on Jan. 13, 2011, and Korean Patent Application No 10-2011-0049932 filed in the Korean Intellectual Property Office on May 26, 2011, and the entire contents of which are incorporated herein by reference.

BACKGROUND OF THE INVENTION (a) Field of the Invention

The present invention relates to a process for the preparation of phenyl carbamate derivatives, useful in the treatment of CNS (central nervous system) disorders. The present invention further relates to a process for preparation of intermediates in the synthesis of the phenyl carbamate derivatives.

(b) Description of the Related Art

CNS (central nervous system) disorders nowadays concern large sections of the population. In particular on account of the increase in elderly people, the numbers of patients are increasing continuously.

Myotony or spasm, which is one of the CNS disorders, is frequently observed as a sequel of cerebrovascular disorders such as stroke or a sequel of head injuries, and is not easy to treat. Myotony or spasm is one of skeletal muscle dysfunction diseases due to an increase of muscle tone, and caused by central nervous system damage due to various causes such as external injury, cerebrovascular accidents, and the like. The muscle tension is caused by various causes, for example, cervicoomobrachial syndrome which is caused by abnormal posture, fatigue, age-related spine deformity, and the like, and causes spasticity or pain in skeletal muscles of the neck, shoulders, arms, waist, and back; spastic paralysis causing the disability of voluntary movement due to muscle hypertonia of hands and feet by disorder of central nervous system such as cerebrovascular disorder; and a combination thereof, thereby resulting in serious hindrances to normal life.

In particular, spastic paralysis is a serious disorder with accompanying symptoms including muscle tension and/or muscular stiffness of hands and feet, difficulty in walking, and the like, thererby causing serious hindrances to normal life. Centrally acting muscle relaxants relieve muscle tension by blocking receptors associated with the stimulation of muscular function or stimulating receptors associated with inhibiting muscular function, or reducing excessively activated reflex function.

Such centrally acting muscle relaxants may include Methocarbaamol, Chlormezanon, Carisoprodol, Eperisone, Phenprobamide, and the like. However, these drugs act on interneuron of the spinal cord, thereby inhibiting monosynaptic and polysynaptic reflexes, and thus, may cause side effects, such as central nervous inhibition, muscle weakness, and the like. Therefore, there is clearly a need for improved medication.

SUMMARY OF THE INVENTION

One embodiment provides a process of preparing a novel organic compound, phenyl carbamate derivatives. More particularly, a process of the preparation of a compound of Chemical Formula 1 is provided:

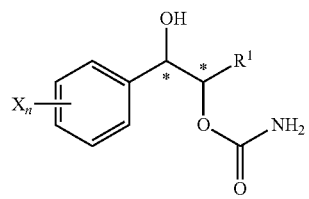

[Chemical Formula 1]

wherein X is one or more independently selected from halogens, preferably chlorine; n, that means the number of substituent X, is an integer from 1 to 5, in particular, 1 or 2; and R' is selected from the group consisting of a linear or branched alkyl group having 1-10 carbon atoms, in particular 1-4 carbon atoms. In this compound, 2 chiral carbons exist at positions 1 and 2 from phenyl group substituted with X; the compound may exist in the form of an enantiomer, a diastereomer, a mixture of enantiomers, or a mixture of diastereomers, as well as a racemate. Another embodiment provides an intermediate to produce the phenyl carbamate compound of Chemical Formula 1.

DETAILED DESCRIPTION OF THE EMBODIMENTS

Continuing its research work in the field of the treatment of CNS disorders, the present inventors found that substituted phenyl carbamate derivatives of the following Chemical Formula 1 exhibit remarkably excellent treatment activity on CNS disorders, example muscle relaxation, in various screening models and simultaneously has very low toxicity, to complete the invention.

The process is directed to improvement in the manufacture of substituted phenyl carbamate derivatives which would be industrially feasible, facilitate, simple, and cost-effective manufacture of phenyl carbamate derivatives.

A process of the preparation of a compound of Chemical Formula 1 is provided:

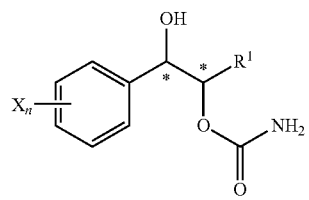

(Chemical Formula 1)

wherein X is one or more independently selected from halogens, preferably chlorine; n, that means the number of substituent X, is an integer from 1 to 5, in particular, 1 or 2; and $R^1$ is selected from the group consisting of a linear or branched alkyl group having 1-10 carbon atoms, in particular 1-4 carbon atoms.

In this compound, 2 chiral carbons exist at positions 1 and 2 from phenyl group substituted with X; the compound may exist in the form of an enantiomer, a diastereomer, a mixture of enantiomers, or a mixture of diastereomers, as well as a racemate.

The process is able to achieve a remarkably excellent productivity as well as cost-effective manufacture of phenyl carbamate derivatives. The compound of Chemical Formula 1 obtained by the process is suitable as a drug especially in the treatment of in the CNS disorders.

More specifically, the process of the preparation of a compound of Chemical Formula 1 may comprise the step of performing a carbamation of a compound of Chemical Formula 6 by reacting the compound of Chemical Formula 6 with chlorosulfonyl isocyanate, to produce a phenyl carbamate compound of Chemical Formula 1:

(Chemical Formula 6)

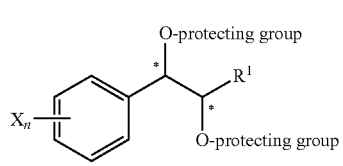

The process may further comprise the step of protecting a diol compound of Chemical Formula 5 by introducing a protecting group into the diol compound, to produce a compound of Chemical Formula 6, prior to the carbamation step:

(Chemical Formula 5)

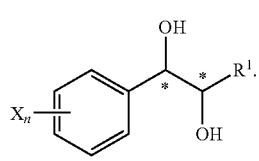

The process may further comprise the step of performing dihydroxylation of a trans olefin compound of Chemical Formula 4, to produce the diol compound of Chemical Formula 5, prior to the protection step:

(Chemical Formula 4)

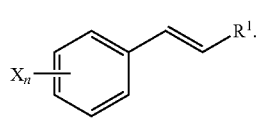

The process may further comprise the step of producing the trans olefin compound of Chemical Formula 4 by reacting a compound of Chemical Formula 2 and a compound of Chemical Formula 3:

(Chemical Formula 2)

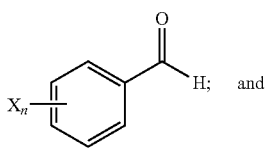

and (Chemical Formula 3)

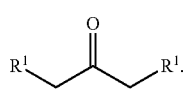

In a concrete embodiment, the process may include the step of:

(1) reacting a compound of Chemical Formula 2 and a compound of Chemical Formula 3 to produce a trans olefin compound of Chemical Formula 4:

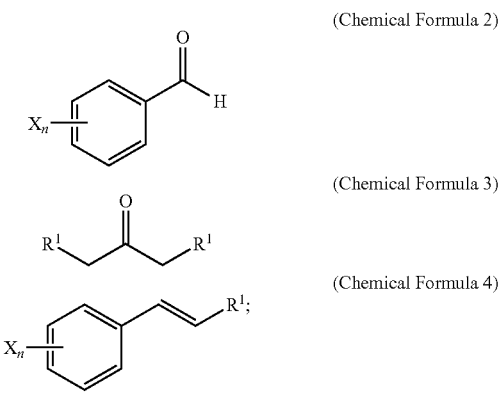

(2) performing dihydroxylation of the produced trans olefin compound of Chemical Formula 4, to produce a diol compound of Chemical Formula 5:

(Chemical Formula 5)

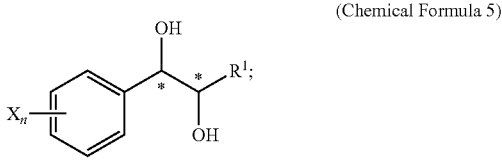

(3) protecting the produced diol compound of Chemical Formula 5 by introducing a protecting group into the diol compound, to produce a compound of Chemical Formula 6:

(Chemical Formula 6)

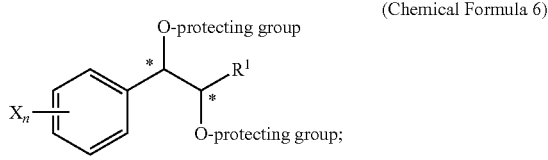

and (4) performing a carbamation reaction of the compound of Chemical Formula 6 by reacting the compound of Chemical Formula 6 with chlorosulfonyl isocyanate, to produce a phenyl carbamate compound of Chemical Formula 1.

The definitions of the substituents 'X', 'n', and '$R^1$' are as described above.

Steps (1) and (2) may be illustrated by following Reaction Formula 1:

(Reaction Formula I: Synthesis of Diol-1)

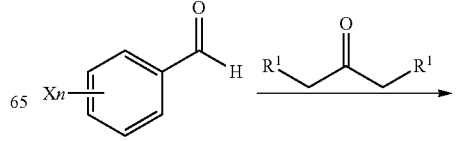

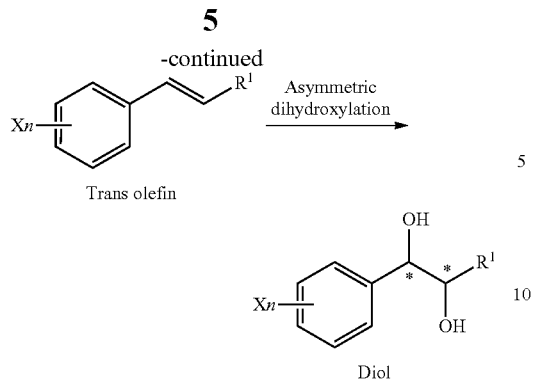

Trans olefin

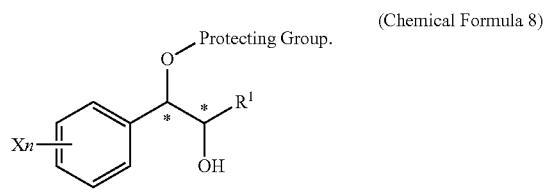

Diol

A diol compound, that has an optical activity and can be used in the synthesis of a carbamate compound, may be synthesized by dihydroxylation of a trans-olefin compound. The dihydroxylation may be performed using a sharpless asymmetric dihydroxylation catalyst. The asymmetric dihydroxylation catalyst may be one or more selected from the group consisting of a chiral ligand (e.g., $(DHQD)_2PHAL$, $(DHQ)_2PHAL$, etc.), an osmium catalyst (e.g., $OsO_4$, $K_2OsO_2(OH)_4$, etc.), $K_2CO_3$, $K_3Fe(CN)_6$, N-methylmorpholine oxide (NMO), methane sulfone amide ($CH_3SO_2NH_2$), and the like. For example, the asymmetric dihydroxylation catalyst may be AD-mix-α ($K_2OsO_2(OH)_4$(cat), $K_2CO_3$, $K_3Fe(CN)_6$, $(DHQ)_2PHAL$(cat)) and methane sulfone amide ($CH_3SO_2NH_2$), or $OsO_4$ and N-methylmorpholine oxide (NMO). The dihydroxylation may be performed for 3 to 12 hours (e.g., overnight) at 0 to 5° C.

Another optically active substance of diol may be synthesized using a reduction agent after synthesizing a hydroxyketone compound using Haloro-Mandelic acid. The reduction agent may be any conventional reduction agent in synthesis of a diol compound; for example, the reduction agent may be one or more selected from the group consisting of $Zn(BH_4)_2$(Zincborohydride), $AlH_3$(Aluminiumhydride), DIBAL (Diisobutylaluminiumhydride), Red-Al(Sodium bis (2-mehtoxyethoxy)aluminium hydride), and the like, but not be limited thereto.

Alternatively, the diol compound of Chemical Formula 5 may be synthesized from a protected alcohol compound of Chemical Formula 8 by deprotection thereof. Therefore, the process may further comprise the step of deprotecting a protected alcohol compound of Chemical Formula 8, to produce the diol compound of Chemical Formula 5, prior to the protection step:

(Chemical Formula 8)

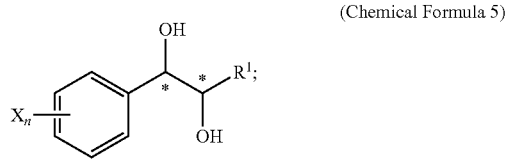

The protected alcohol compound of Chemical Formula 8 may be synthesized from a compound of Chemical Formula 7 by reduction thereof. Therefore, the process may further comprise the step of reducing a compound of Chemical Formula 7, to produce the protected alcohol compound of Chemical Formula 8, prior to the deprotection step:

(Chemical Formula 7)

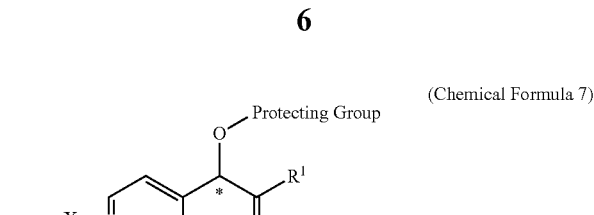

In a concrete embodiment, the process may include the step of:

(i) reducing a compound of Chemical Formula 7, to produce a protected alcohol compound of Chemical Formula 8:

(Chemical Formula 7)

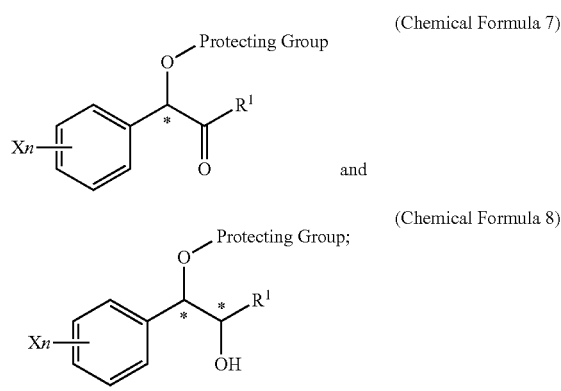

and (Chemical Formula 8)

(ii) deprotecting the protected alcohol compound of Chemical Formula 8, to produce a diol compound of Chemical Formula 5:

(Chemical Formula 5)

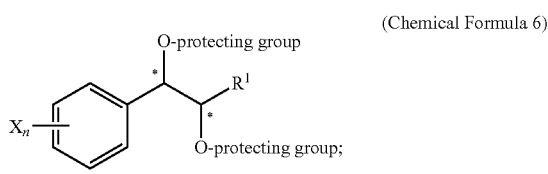

(iii) protecting the produced diol compound of Chemical Formula 5 by introducing a protecting group into the diol compound, to produce a compound of Chemical Formula 6:

(Chemical Formula 6)

and (iv) performing a carbamation reaction of the compound of Chemical Formula 6 by reacting the compound of Chemical Formula 6 with chlorosulfonyl isocyanate, to produce a phenyl carbamate compound of Chemical Formula 1.

Steps (i) and (ii) may be illustrated by following Reaction Formula II:

(Reaction Formula II: Synthesis of Diol-2)

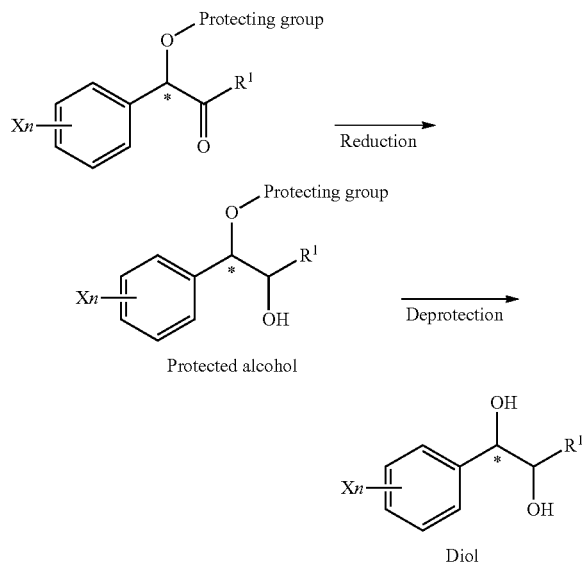

For example, the diol compound of Chemical Formula 5 may be synthesized by the following Reaction Formula II-1:

(Reaction Formula II-1)

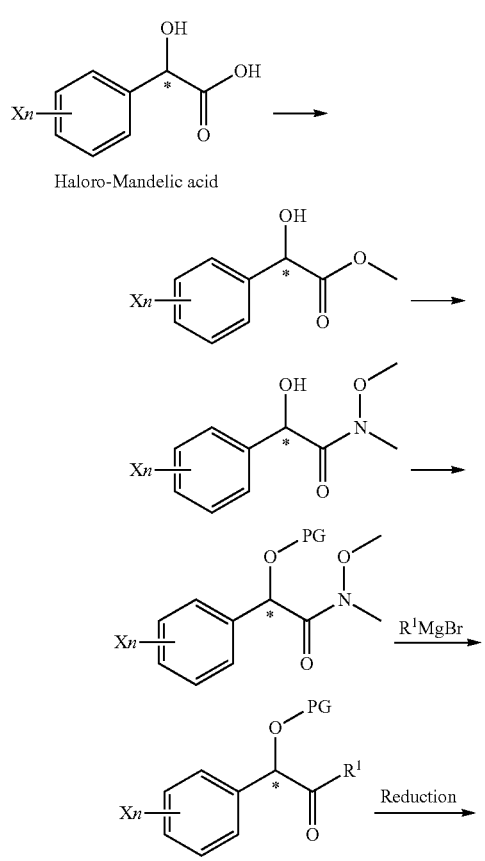

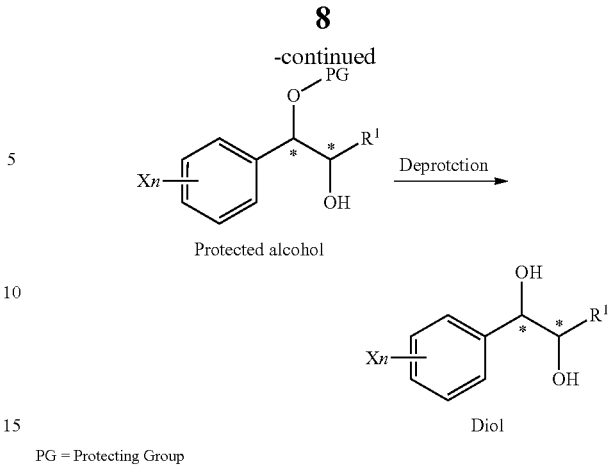

PG = Protecting Group

The definitions of the substituents 'X', 'n', and '$R^1$' in Chemical Formula 7 and 8 are as described above.

The protecting group present in Chemical Formula 7 and 8 may be any alcohol-protecting group, for example, one or more selected from the group consisting of Trialkyl Silyl group (e.g., TMS, TES, TIPS, and the like), Ether group[e.g., MOM (Methoxymethyl ether), MEM (2-Methoxyethoxymethyl ether), and the like], Ester group[e.g., Ac (acetate), Bz (Benzoate), and the like], and the like, but may not be limited thereto.

Step (3) (or step (iii)) and step (4) (or step (iv)) may be illustrated by the following Reaction Formula III:

Reaction Formula III: Carbamation Reaction-1

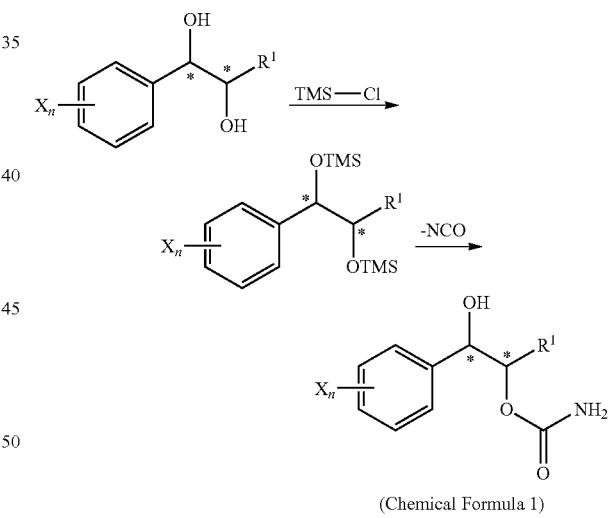

(Chemical Formula 1)

In order to achieve a high selectivity form of regioisomer of single carbamate of diol having halogen substituent at phenyl ring (Chemical Formula 1), a protecting group may be introduced into the diol compound of Chemical Formula 5, and a carbamation reaction is performed using an isocyanate (—N═C═O) based compound, such as chlorosulfonyl isocyanate (Cl—$SO_2$NCO), to synthesize a single carbamate compound as represented by Chemical Formula 1. The each reaction may be performed under the temperature from −5° C. to 5° C., in particular about 0° C., for 1 to 7 hours.

The protecting group present in Chemical Formula 6 may be any alcohol-protecting group, for example, one or more selected from the group consisting of a trialkyl silyl group, wherein each alkyl is independently selected from linear or branched C1-C4 alkyls, such as a trimethyl silyl group (TMS), triisopropyl silyl (TIPS), t-butyl dimethyl silyl (TBDMS), and the like; t-butyl diphenyl silyl (TBDPS); trialkyl silyl ether group, wherein each alkyl is independently selected from linear or branched C1-C4 alkyls; and the like, but may not be limited thereto.

One concrete embodiment, trimethyl silyl group (TMS) may be employed as a protecting group, to produce a compound of Chemical Formula 6-1 as follows:

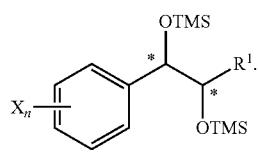

(Chemical Formula 6-1)

The process is capable of an industrially feasible, facilitate, simple, and cost-effective manufacture of phenyl carbamate derivatives of Chemical Formula 1 that is useful in the treatment of CNS disorders in high yield.

Alternatively, the phenyl carbamate derivative of Chemical Formula 1 may be synthesized from a protected carbamate compound of Chemical Formula 9 by deprotection thereof. Therefore, in another embodiment, the process of preparing a phenyl carbamate derivative of Chemical Formula 1 may comprise the step of deprotecting a protected carbamate compound of Chemical Formula 9:

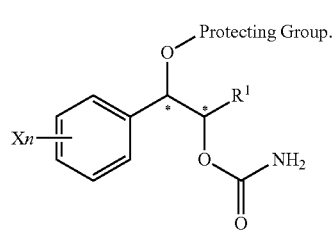

(Chemical Formula 9)

The protected carbamate compound of Chemical Formula 9 may be synthesized from the produce the protected alcohol compound of Chemical Formula 8 by carbamation thereof. Therefore, the process may further comprise the step of performing a carbamation of a protected alcohol compound of Chemical Formula 8, to produce the protected carbamate compound of Chemical Formula 9, prior to the deperotecting step:

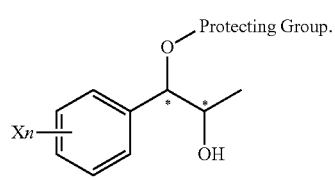

(Chemical Formula 8)

In a concrete embodiment, the process may include the step of:

(a) performing a carbamation of a protected alcohol compound of Chemical Formula 8, to produce a protected carbamate compound of Chemical Formula 9:

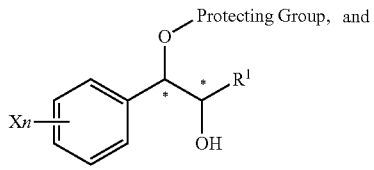

(Chemical Formula 8)

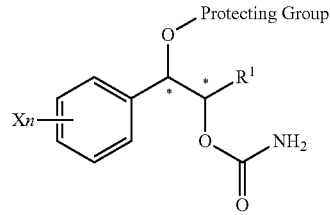

(Chemical Formula 9)

and (b) deprotecting the protected carbamate compound of Chemical Formula 9, to produce a phenyl carbamate compound of Chemical Formula 1.

Steps (a) and (b) may be illustrated by the following Reaction Formula IV:

Reaction Formula IV: Carbamation Reaction-2

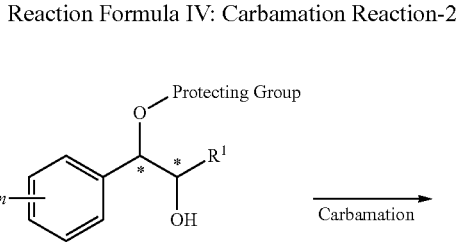

Protected alcohol

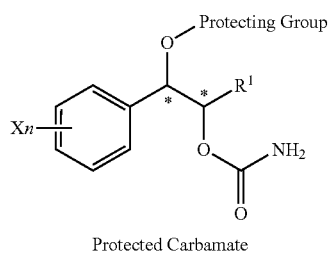

Protected Carbamate

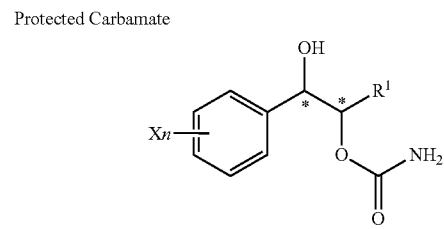

(Chemical Formula 1)

As described above, the protected alcohol compound of Chemical Formula 8 may be synthesized from the compound of Chemical Formula 7 by reduction thereof. Therefore, the process may further comprise the step of reducing a compound of Chemical Formula 7, to produce the protected alcohol compound of Chemical Formula 8, prior to the carbamation step:

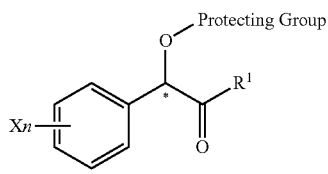

(Chemical Formula 7)

The definitions of the substituents 'X', 'n', and 'R¹' in Chemical Formula 7, 8 and 9 are as described above.

The protecting group present in Chemical Formula 7, 8 and 9 may be any alcohol-protecting group, for example, one or more selected from the group consisting of Trialkyl Silyl group (e.g., TMS, TES, TIPS, and the like), Ether group [e.g., MOM (Methoxymethyl ether), MEM (2-Methoxyethoxymethyl ether), and the like], Ester group [e.g., Ac (acetate), Bz (Benzoate), and the like], and the like, but may not be limited thereto.

Another embodiment provides a compound of Chemical Formula 6 as an intermediate to produce the phenyl carbamate compound of Chemical Formula 1.

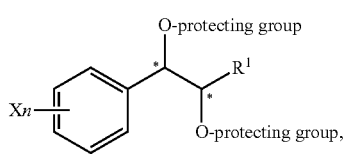

(Chemical Formula 6)

wherein X is one or more independently selected from halogens, preferably chlorine; n, that means the number of substituent X, is an integer from 1 to 5, in particular, 1 or 2; $R^1$ is selected from the group consisting of a linear or branched alkyl group having 1-10 carbon atoms, in particular 1-4 carbon atoms; and the protecting group is one or more selected from the group consisting of a trialkyl silyl group, wherein each alkyl is independently selected from linear or branched C1-C4 alkyls, such as a trimethyl silyl group (TMS), triisopropyl silyl (TIPS), t-butyl dimethyl silyl (TBDMS), and the like; t-butyl diphenyl silyl (TBDPS); trialkyl silyl ether group, wherein each alkyl is independently selected from linear or branched C1-C4 alkyls; and the like.

Another embodiment provides a process of the preparation of a compound of Chemical Formula 6, comprising the step of protecting a diol compound of Chemical Formula 5 by introducing a protecting group into the diol compound, to produce the compound of Chemical Formula 6:

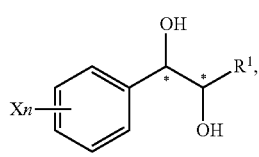

(Chemical Formula 5)

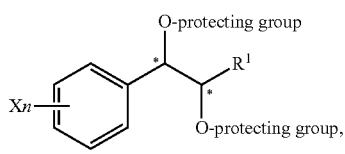

(Chemical Formula 6)

wherein X is one or more independently selected from halogens, preferably chlorine; n, that means the number of substituent X, is an integer from 1 to 5, in particular, 1 or 2; $R^1$ is selected from the group consisting of a linear or branched alkyl group having 1-10 carbon atoms, in particular 1-4 carbon atoms; and the protecting group is one or more selected from the group consisting of a trialkyl silyl group, wherein each alkyl is independently selected from linear or branched C1-C4 alkyls, such as a trimethyl silyl group (TMS), triisopropyl silyl (TIPS), t-butyl dimethyl silyl (TBDMS), and the like; t-butyl diphenyl silyl (TBDPS); trialkyl silyl ether group, wherein each alkyl is independently selected from linear or branched C1-C4 alkyls; and the like.

Another embodiment provides a compound of Chemical Formula 7, Chemical Formula 8, or Chemical Formula 9, as an intermediate to produce the phenyl carbamate compound of Chemical Formula 1:

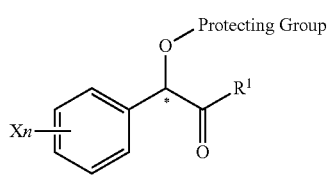

(Chemical Formula 7)

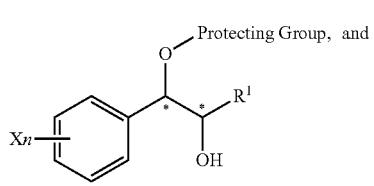

(Chemical Formula 8)

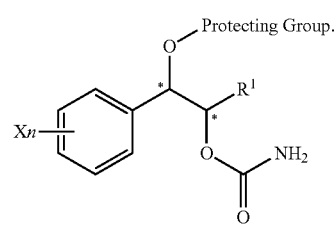

(Chemical Formula 9)

Another embodiment provides a process of the preparation of a protected alcohol compound of Chemical Formula 8, comprising the step of reducing a compound of Chemical Formula 7, to produce the protected alcohol compound of Chemical Formula 8.

Still another embodiment provides a process of the preparation of a protected carbamate compound of Chemical Formula 9, comprising the step of performing a carbamation of a protected alcohol compound of Chemical Formula 8, to produce the protected carbamate compound of Chemical Formula 9. The process may further comprise the step of reducing a compound of Chemical Formula 7, to produce the protected alcohol compound of Chemical Formula 8, prior to the carbamation step.

The definitions of the substituents 'X', 'n', and 'R¹' in Chemical Formula 7, 8 and 9 are as described above.

The protecting group present in Chemical Formula 7, 8 and 9 may be any alcohol-protecting group, for example, one or more selected from the group consisting of Trialkyl Silyl group (e.g., TMS, TES, TIPS, and the like), Ether group [e.g., MOM (Methoxymethyl ether), MEM (2-Methoxyethoxymethyl ether), and the like], Ester group [e.g., Ac (acetate), Bz (Benzoate), and the like], and the like, but may not be limited thereto.

EXAMPLE

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

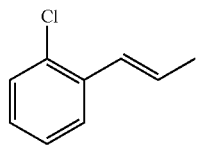

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%). $^1$H NMR (400 MHz, $CDCl_3$) δ1.94 (d, J=4.8 Hz, 3H), 6.24 (m, 1H), 6.78 (d, J=14 Hz, 1H), 7.11~7.51 (m, 4H)

Preparation Example 2

Synthesis of 1-(2-chlorophenyl)-trans-1-butene

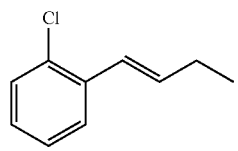

The substantially same method as described in Preparation Example 1 was conducted, except that 3-heptanone was used instead of 3-pentanone, to obtain the title compound (2.9 g, yield 83%).

$^1$H NMR (400 MHz, $CDCl_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.13~7.54 (m, 4H)

Preparation Example 3

Synthesis of 1-(2-chlorophenyl)-3-methyl-trans-1-butene

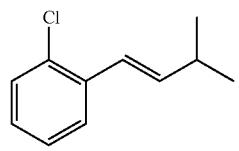

The substantially same method as described in Preparation Example 1 was conducted, except that 2,6-dimethyl-heptan-4-one was used instead of 3-pentanone, to obtain the title compound (8.0 g, yield 50~90%).

$^1$H NMR (400 MHz, $CDCl_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.12~7.54 (m, 4H)

Preparation Example 4

Synthesis of 1-(2-chlorophenyl)-trans-1-hexene

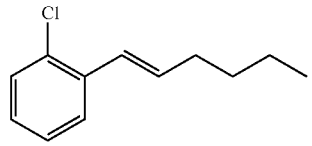

The substantially same method as described in Preparation Example 1 was conducted, except that 6-undecanone was used instead of 3-pentanone, to obtain the title compound (10 g, yield 85%).

$^1$H NMR (400 MHz, $CDCl_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.13~7.54 (m, 4H)

Preparation Example 5

Synthesis of 1-(2,4-dichlorophenyl)-trans-1-propene

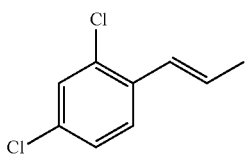

The substantially same method as described in Preparation Example 1 was conducted, except that 2,4-dichlorobenzenaldehyde was used instead of 2-chlorobenzenaldehyde, to obtain the title compound (2.4 g, yield 57%).

¹H NMR (400 MHz, CDCl₃) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 6

Synthesis of 1-(2,4-dichlorophenyl)-trans-1-butene

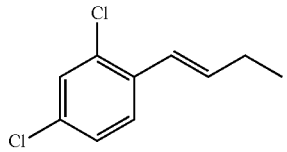

The substantially same method as described in Preparation Example 5 was conducted, except that 3-heptanone was used instead of 3-pentanone, to obtain the title compound (2.1 g, yield 90%).
¹H NMR (400 MHz, CDCl₃) δ1.14 (d, J=7.6 Hz, 3H), 2.20~2.33 (m, 2H), 6.26 (dt, J=16 Hz, 6.8 Hz, 1H), 6.70 (d, J=15.6 Hz, 1H), 7.18~7.46 (m, 3H)

Preparation Example 7

Synthesis of 1-(2,6-dichlorophenyl)-3-methyl-trans-1-butene

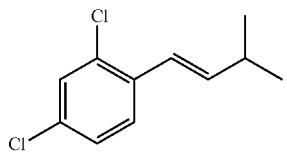

The substantially same method as described in Preparation Example 5 was conducted, except that 2,6-dimethyl-heptan-4-one was used instead of 3-pentanone, to obtain the title compound (0.23 g, yield 10~40%).
¹H NMR (400 MHz, CDCl₃) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.18~7.46 (m, 3H)

Preparation Example 8

Synthesis of 1-(2,4-dichlorophenyl)-trans-1-hexene

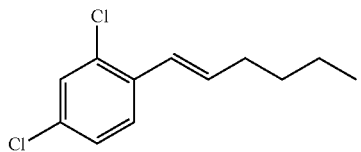

The substantially same method as described in Preparation Example 5 was conducted, except that 6-undecanone was used instead of 3-pentanone, to obtain the title compound (3.2 g, yield 40~80%).

¹H NMR (400 MHz, CDCl₃) δ0.96 (t, J=7.2 Hz, 3H), 1.38~1.52 (m, 4H), 2.25~2.31 (m, 2H), 6.22 (dt, J=15.6 Hz, 6.8 Hz, 1H), 6.70 (d, J=15.6 Hz, 1H), 7.18~7.46 (m, 3H)

Preparation Example 9

Synthesis of 1-(2,6-dichlorophenyl)-trans-1-propene

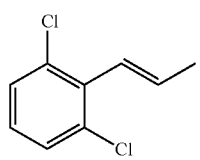

The substantially same method as described in Preparation Example 1 was conducted, except that 2,6-dichlorobenzenaldehyde was used instead of 2-chlorobenzenaldehyde, to obtain the title compound (0.4 g, yield 10~40%).
¹H NMR (400 MHz, CDCl₃) δ1.98 (d, J=8 Hz, 3H), 6.23~6.31 (m, 1H), 6.40 (d, J=16 Hz, 1H), 7.05~7.32 (m, 3H)

Preparation Example 10

Synthesis of 1-(2,6-dichlorophenyl)-trans-1-butene

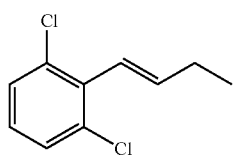

The substantially same method as described in Preparation Example 9 was conducted, except that 3-heptanone was used instead of 3-pentanone, to obtain the title compound (1.2 g, yield 10~40%).
¹H NMR (400 MHz, CDCl₃) δ1.17 (t, J=7.6 Hz, 3H), 2.30~2.37 (m, 2H), 6.29 (dt, J=16.4 Hz, 6 Hz, 1H), 6.37 (d, J=16.4 Hz, 1H), 7.05~7.32 (m, 3H)

Preparation Example 11

Synthesis of 1-(2,6-dichlorophenyl)-3-methyl-trans-1-butene

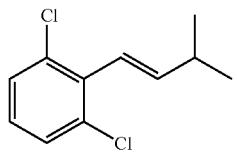

The substantially same method as described in Preparation Example 9 was conducted, except that 2,6-dimethyl-heptan-4-one was used instead of 3-pentanone, to obtain the title compound (0.23 g, yield 10~40%).

$^{1}$H NMR (400 MHz, CDCl$_{3}$) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.05~7.32 (m, 3H)

Preparation Example 12

Synthesis of 1-(2,6-dichlorophenyl)-trans-1-hexene

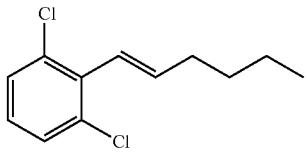

The substantially same method as described in Preparation Example 9 was conducted, except that 6-undecanone was used instead of 3-pentanone, to obtain the title compound (0.2 g, yield 10~40%).

$^{1}$H NMR (400 MHz, CDCl$_{3}$) δ0.99 (t, J=7.2 Hz, 3H), 1.14~1.59 (m, 4H), 2.30~2.36 (m, 2H), 6.24 (dt, J=16 Hz, 6.6 Hz, 1H), 6.38 (d, J=16.4 Hz, 1H), 7.05~7.33 (m, 3H)

Preparation Example 13

Synthesis of 1-(2,3-dichlorophenyl)-trans-1-propene

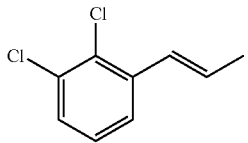

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^{1}$H NMR (400 MHz, CDCl$_{3}$) δ1.94 (d, J=4.8 Hz, 3H), 6.24 (m, 1H), 6.78 (d, J=14 Hz, 1H), 7.11~7.51 (m, 3H)

Preparation Example 14

Synthesis of 1-(2-chlorophenyl)-(S,S)-1,2-propanediol

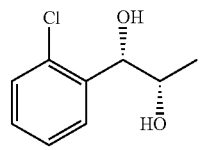

1-(2-chlorophenyl)-trans-1-propene (1.5 g, Preparation Example 1) was dissolved in 30 mL of the mixture of t-BuOH/H$_{2}$O (1:1 (V/V)). At 0° C., AD-mix-α (Aldrich, U.S.A.) (13.7 g) and methane sulfone amide (CH$_{3}$SO$_{2}$NH$_{2}$, 0.76 g, 0.0080 mol) were added thereto and stirred for overnight. When the reaction was completed, the obtained product was washed with an aqueous solution of sodium sulfite (Na$_{2}$SO$_{3}$) and ethylacetate (EA). Then, the organic layer was dehydrated with anhydrous magnesium sulfate (MgSO$_{4}$), filtrated, and concentrated under reduced pressure. The concentrated residue was purified by a silica gel column chromatography to produce the title compound (1.65 g, yield 90%).

$^{1}$H NMR (400 MHz, CDCl$_{3}$) δ1.20 (d, J=6.4 Hz, 3H), 2.48 (d, J=4.0 Hz 1H), 2.92 (d, J=4.4 Hz, 1H), 3.93~3.97 (m, 1H), 4.97 (t, J=4.8 Hz, 1H), 7.22~7.51 (m, 4H)

$^{13}$CNMR (100 MHz, CDCl$_{3}$) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

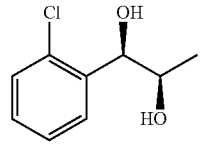

1-(2-chlorophenyl)-trans-1-propene (2.5 g, Preparation Example 1) was dissolved in 50 mL of the mixture of t-BuOH/H$_{2}$O (1:1 (V/V)). At 0° C., AD-mix-α (Aldrich, U.S.A.) (23.5 g) and methane sulfone amide (CH$_{3}$SO$_{2}$NH$_{2}$, 1.27 g, 0.013 mol) were added thereto and stirred for overnight. When the reaction was completed, the obtained product was washed with an aqueous solution of sodium sulfite (Na$_{2}$SO$_{3}$) and ethylacetate (EA). Then, the organic layer was dehydrated with anhydrous magnesium sulfate (MgSO$_{4}$), filtrated, and concentrated under reduced pressure. The concentrated residue was purified by a silica gel column chromatography to produce the title compound (2.96 g, yield 90%).

$^{1}$H NMR (400 MHz, CDCl$_{3}$) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 16

Synthesis of the mixture of 1-(2-chlorophenyl)-(S,S)-1,2-propanediol and 1-(2-chlorophenyl)-(R,R)-1,2-propanediol

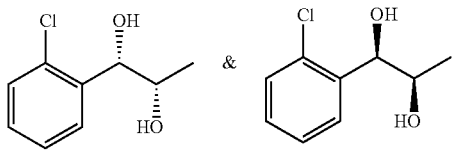

1-(2-chlorophenyl)-trans-1-propene (6.53 g, Preparation Example 1) was dissolved in 45 mL of the mixture of acetone/t-BuOH/H$_{2}$O (5:1:1 V/V). At the room temperature, N-methylmorpholine-N-oxide (7.51 g) and OsO$_{4}$ (0.54 g) were added thereto and stirred for 2~3 hours. When the reaction was completed, the obtained product was washed with water and methylenechloride (MC). Then, the organic layer was dehydrated with anhydrous magnesium sulfate (MgSO$_{4}$), filtrated, and concentrated under reduced pressure. The concentrated residue was purified by a silica gel column chromatography to produce the title compound (6.42 g, yield 80%).

¹H NMR (400 MHz, CDCl₃) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 17

Synthesis of 1-(2-chlorophenyl)-(S,S)-1,2-butanediol

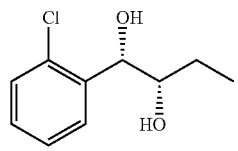

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 18

Synthesis of 1-(2-chlorophenyl)-(R,R)-1,2-butanediol

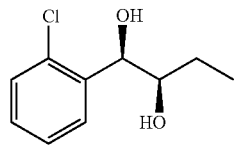

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 19

Synthesis of the mixture of 1-(2-chlorophenyl)-(S,S)-1,2-butanediol and 1-(2-chlorophenyl)-(R,R)-1,2-butanediol

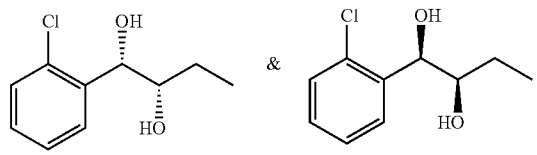

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

¹H NMR (400 MHz, CDCl₃) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 20

Synthesis of 1-(2-chlorophenyl)-3-methyl-(S,S)-1,2-butanediol

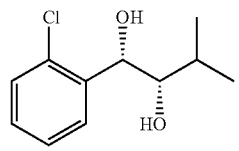

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

¹H NMR (400 MHz, CDCl₃) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 21

Synthesis of 1-(2-chlorophenyl)-3-methyl-(R,R)-1,2-butanediol

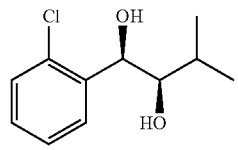

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR (400 MHz, CDCl$_3$) δ1.07 (t, J=7.2 Hz, 6H), 1.82~1.90 (m, 1H), 1.93 (d, J=5.6 Hz, 1H), 2.79 (d, J=6 Hz, 1H), 3.53~3.57 (m, 1H), 5.23~5.25 (m, 1H), 7.23~7.54 (m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

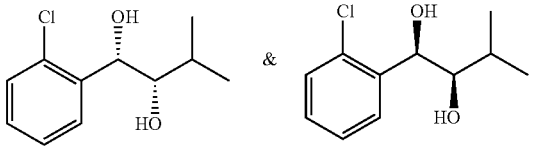

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).
$^1$H NMR (400 MHz, CDCl$_3$) δ1.07 (t, J=7.2 Hz, 6H), 1.83~1.90 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 23

Synthesis of 1-(2-chlorophenyl)-(S,S)-1,2-hexanediol

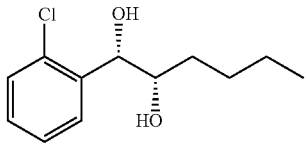

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).
$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.23~7.53 (m, 4H)

Preparation Example 24

Synthesis of 1-(2-chlorophenyl)-(R,R)-1,2-hexanediol

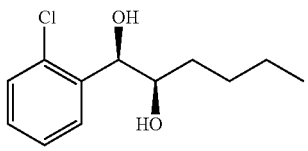

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).
$^1$H NMR (400 MHz, CDCl$_3$) δ0.91 (t, J=6.6 Hz, 3H), 1.35~1.65 (m, 6H), 2.08 (d, J=4.8 Hz, 1H), 2.70 (d, J=5.2 Hz, 1H), 3.80~3.83 (m, 1H), 5.05 (t, J=5.0 Hz, 1H), 7.24~7.56 (m, 4H)

Preparation Example 25

Synthesis of the mixture of 1-(2-chlorophenyl)-(S,S)-1,2-hexanediol and 1-(2-chlorophenyl)-(R,R)-1,2-hexanediol

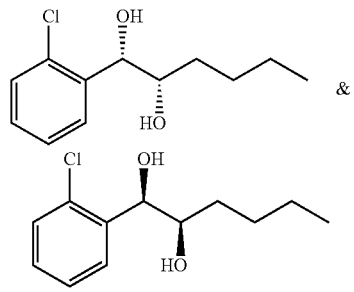

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).
$^1$H NMR (400 MHz, CDCl$_3$) δ0.90 (t, J=7.2 Hz, 3H), 1.26~1.55 (m, 6H), 2.08 (d, J=4.4 Hz, 1H), 2.71 (d, J=5.6 Hz, 1H), 3.78~3.84 (m, 1H), 5.04 (t, J=3.2 Hz, 1H), 7.24~7.55 (m, 4H)

Preparation Example 26

Synthesis of 1-(2,4-dichlorophenyl)-(S,S)-1,2-propanediol

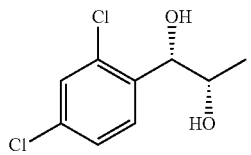

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).
$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 27

Synthesis of
1-(2,4-dichlorophenyl)-(R,R)-1,2-propanediol

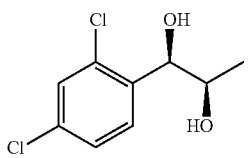

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

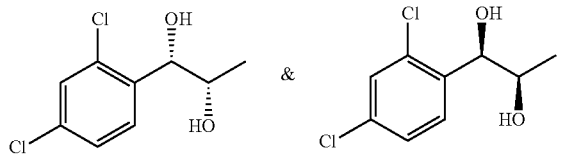

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 29

Synthesis of
1-(2,4-dichlorophenyl)-(S,S)-1,2-butanediol

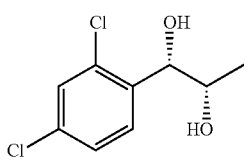

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR (400 MHz, CDCl$_3$) δ1.02 (t, J=7.4 Hz, 3H), 1.54~1.61 (m, 2H), 2.07 (d, J4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 30

Synthesis of
1-(2,4-dichlorophenyl)-(R,R)-1,2-butanediol

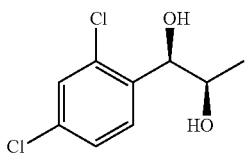

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR (400 MHz, CDCl$_3$) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

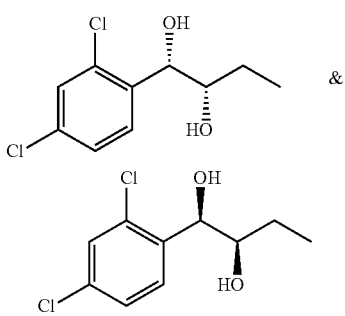

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

¹H NMR (400 MHz, CDCl₃) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 77.31~7.49 (m, 3H)

Preparation Example 32

Synthesis of 1-(2,4-dichlorophenyl)-3-methyl-(S,S)-1,2-butanediol

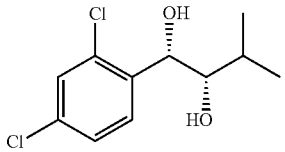

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 33

Synthesis of 1-(2,4-dichlorophenyl)-3-methyl-(R,R)-1,2-butanediol

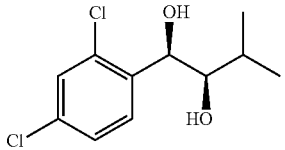

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

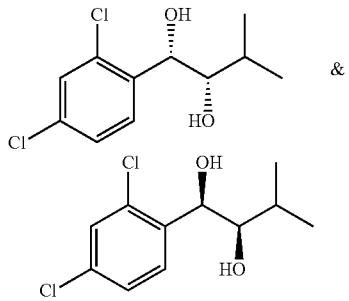

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 35

Synthesis of 1-(2,4-dichlorophenyl)-(S,S)-1,2-hexanediol

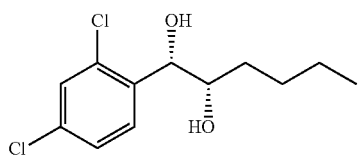 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.1 g, yield 60~90%).

¹H NMR (400 MHz, CDCl₃) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 36

Synthesis of 1-(2,4-dichlorophenyl)-(R,R)-1,2-hexanediol

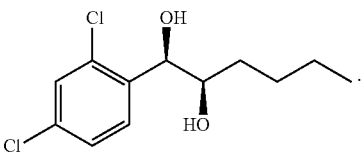 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.2 g, yield 60~95%).

¹H NMR (400 MHz, CDCl₃) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

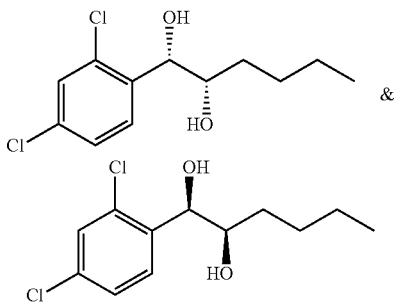

The substantially same method as described in Preparation Example 16 was conducted, except that 1-(2,4-dichlorophenyl)-trans-1-propene (Preparation Example 8) was used instead of 1-(2-chlorophenyl)-trans-1-propene (Preparation Example 1), to obtain the title compound (0.67 g, yield 60~95%).

$^1$H NMR (400 MHz, CDCl$_3$) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 38

Synthesis of 1-(2,6-dichlorophenyl)-(S,S)-1,2-propanediol

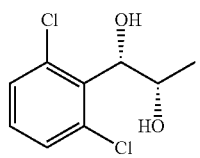

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 39

Synthesis of 1-(2,6-dichlorophenyl)-(R,R)-1,2-propanediol

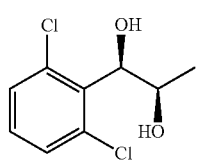

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), J=8.8 Hz, 1H), 7.18~7.36 (m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

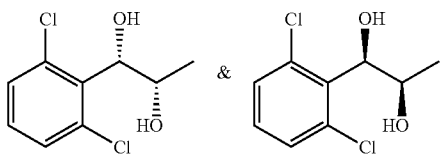

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 41

Synthesis of 1-(2,6-dichlorophenyl)-(S,S)-1,2-butanediol

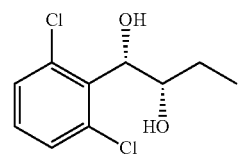

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

$^1$H NMR (400 MHz, CDCl$_3$) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 42

Synthesis of 1-(2,6-dichlorophenyl)-(R,R)-1,2-butanediol

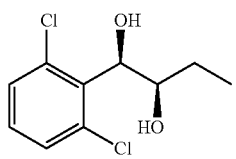

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

$^1$H NMR (400 MHz, CDCl$_3$) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

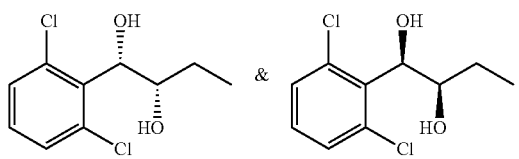

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR (400 MHz, CDCl$_3$) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 44

Synthesis of 1-(2,6-dichlorophenyl)-3-methyl-(S,S)-1,2-butanediol

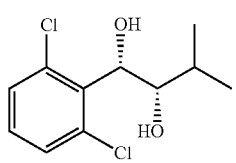

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 45

Synthesis of 1-(2,6-dichlorophenyl)-3-methyl-(R,R)-1,2-butanediol

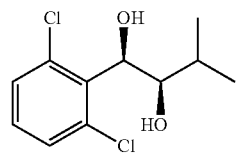

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

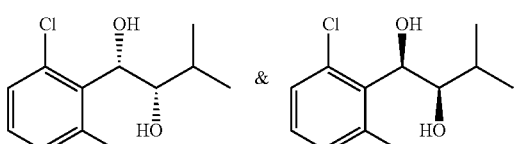

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J 8.4 Hz, 1H), 4.13~4.18 (m, 1H), 5.36 (t, J=7.6 Hz, 1H), 7.17~7.35 (m, 3H)

Preparation Example 47

Synthesis of 1-(2,6-dichlorophenyl)-(S,S)-1,2-hexanediol

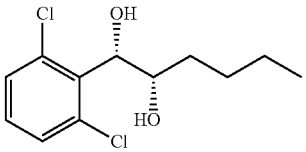 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR (400 MHz, CDCl$_3$) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 48

Synthesis of 1-(2,6-dichlorophenyl)-(R,R)-1,2-hexanediol

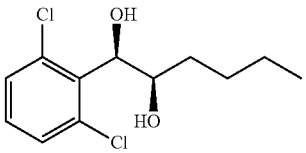 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR (400 MHz, CDCl$_3$) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

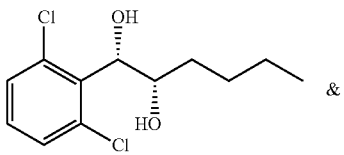

&

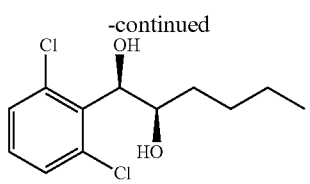

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR (400 MHz, CDCl$_3$) δ0.85 (t, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 50

Synthesis of methyl 2-(2-chlorophenyl)-(R)-2-hydroxyacetate

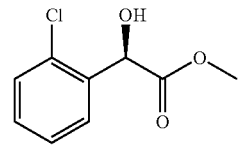

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (15.64 g, yield 95%).

$^1$H NMR (400 MHz, CDCl$_3$) δ 3.59 (d, J=5.2, 1H), 3.79 (t, J=6.0, 3H), 5.59 (d, J=5.2, 1H), 7.28~7.43 (m, 4H)

Preparation Example 51

Synthesis of 2-(2-chlorophenyl)-(R)-2-hydroxy-N-methoxy-N-methylacetamide

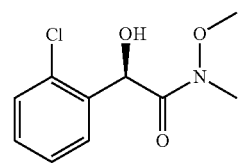

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concentrated under reduced pressure. The concentrated residue was purified by a silica gel column chromatography to produce the title compound (14.68 g, yield 82%).

$^1$H NMR (400 MHz, CDCl$_3$) δ3.23 (s, 3H), 3.28 (s, 3H), 4.33 (d, J=6.0 Hz, 1H), 5.81 (d, J=5.6 Hz, 1H), 7.23~7.42 (m, 4H)

Preparation Example 52

Synthesis of 2-(2-chlorophenyl)-N-methoxy-(R)-2-(methoxymethoxy)-N-methylacetamide

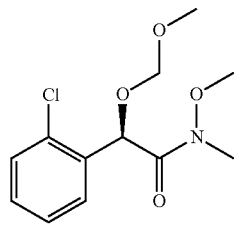 [SMILES: COCO[C@@H](C(=O)N(C)OC)c1ccccc1Cl]

2-(2-chlorophenyl)-(R)-2-hydroxy-N-methoxy-N-methylacetamide (14.68 g) obtained in Preparation Example 51 was dissolved in dichloromethane (DCM, 140 ml), and cooled to 0° C. Diisopropylethylamine (55.67 ml) was slowly added thereto in drop-wise manner, and stirred for 10 minutes. Chloro methyl methyl ether (25.25 ml) was slowly added thereto in drop-wise manner for 30 minutes. After 30 minutes, the ice-bath was removed and the obtained product was stirred for 30 at room temperature. When the reaction was completed, the obtained product was cooled to 0° C. And then, to the obtained product, 1M sodium hydroxide solution (1M NaOH, 20 ml) was added in drop-wise manner, and dichloromethane (DMC) was injected. Then the obtained product was washed with water. The obtained organic layer was dehydrated with anhydrous magnesium sulfate (MgSO$_4$), filtrated, and concentrated under reduced pressure. The concentrated residue was purified by a silica gel column chromatography to produce the title compound (15.57 g, yield 89%).

$^1$H NMR (400 MHz, CDCl$_3$) δ3.19 (s, 3H), 3.42 (s, 3H), 3.47 (s, 3H), 4.75 (d, J=6.8, 1H), 4.81 (d, J=6.8, 1H), 6.07 (s, 1H), 7.27~7.58 (m, 4H)

Preparation Example 53

Synthesis of 1-(2-chlorophenyl)-(R)-1-(methoxymethoxy)propane-2-on

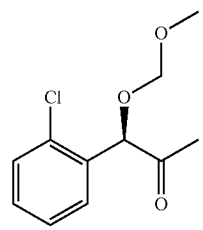

2-(2-chlorophenyl)-N-methoxy-(R)-2-(methoxymethoxy)-N-methylacetamide (15.57 g) obtained in Preparation Example 52 was dissolved in tetrahydrofuran (THF, 150 ml), and cooled to 0° C. 3.0M methyl magnesium bromide (MeMgBr) solution in ether was added thereto in drop-wise manner for 30 minutes, and the obtained product was stirred for 1 hour at 0° C. When the reaction was completed, diethylether (100 ml) was added thereto. The obtained product was washed with 10% (w/v) potassium hydrogen sulfate (KHSO$_4$, 100 ml) and then, washed again with brine. The obtained organic layer was dehydrated with anhydrous magnesium sulfate (MgSO$_4$), filtrated, and concentrated under reduced pressure. The concentrated residue was purified by a silica gel column chromatography to produce the title compound (11.83 g, yield 90%).

$^1$H NMR (400 MHz, CDCl$_3$) δ2.18 (s, 3H), 3.39 (s, 3H), 4.65 (d, J=6.8, 1H), 4.74 (d, J=6.8, 1H), 5.63 (s, 1H), 7.30~7.45 (m, 4H)

Preparation Example 54

Synthesis of 1-(2-chlorophenyl)-(R)-1-(methoxymethoxy)-(S)-2-propanol

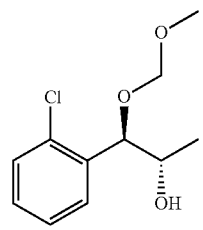

1-(2-chlorophenyl)-(R)-1-(methoxymethoxy)propane-2-on (11.83 g) obtained in Preparation Example 53 was dissolved in toluene (110 ml), and cooled to −40° C. Sodium bis(2-methoxyethoxy)aluminumhydride solution (15.7 ml) in toluene was slowly added thereto for 30 minutes, and then, the obtained product was stirred for 1 hour. When the reaction was completed, the obtained product was washed by slow drop-wise addition of sodium potassium tartrate (100 ml). The obtained organic layer was dehydrated with anhydrous magnesium sulfate (MgSO$_4$), filtrated, and concentrated under reduced pressure. The concentrated residue was purified by a silica gel column chromatography to produce the title compound (10.38 g, yield 87%).

¹H NMR (400 MHz, CDCl₃) δ1.13 (d, J=6.4, 3H), 2.33 (d, J=7.2, 1H), 3.44 (s, 3H), 4.10~4.18 (m, 1H), 4.61 (d, J=6.4, 1H), 4.69 (d, J=6.8, 1H), 5.14 (d, J=3.6, 1H), 7.22~7.55 (m, 4H)

Preparation Example 55

Synthesis of 1-(2-chlorophenyl)-(R,S)-1,2-propanediol

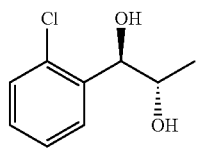

1-(2-chlorophenyl)-(R)-1-(methoxymethoxy)-(S)-2-propanol (10.38 g) obtained in Preparation Example 54 was dissolved in methanol (CH₃OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concentrated under reduced pressure. The concentrated residue was purified by a silica gel column chromatography to produce the title compound (7.05 g, yield 60~90%).

¹H NMR (400 MHz, CDCl₃) δ1.07 (d, J=6.8, 3H), 2.01 (d, J=5.6, 1H), 2.61 (s, 1H), 4.21~4.27 (m, 1H), 5.24 (d, J=3.6, 1H), 7.22~7.64 (m, 4H)

Preparation Example 56

Synthesis of 1-(2-chlorophenyl)-(S,R)-1,2-propanediol

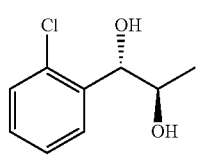

The substantially same method as described in Preparation Example 50~55 was conducted, except that (S)-2-chloromandelic acid was used instead of (R)-2-chloromandelic acid, to obtain the title compound (5.04 g, yield 84%).

¹H NMR (400 MHz, CDCl₃) δ1.07 (d, J=6.8, 3H), 2.00 (d, J=5.6, 1H), 2.54 (d, J=3.6, 1H), 4.22~4.26 (m, 1H), 5.25 (t, J=3.2, 1H), 7.22~7.65 (m, 4H)

Preparation Example 57

Synthesis of 1-(2,3-dichlorophenyl)-(S,S)-1,2-propanediol

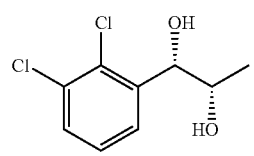

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~ (m, 3H)

Preparation Example 58

Synthesis of 1-(2,3-dichlorophenyl)-(R,R)-1,2-propanediol

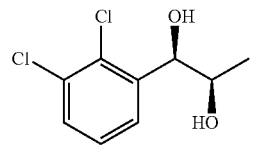

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), J=8.8 Hz, 1H), 7.18~ (m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

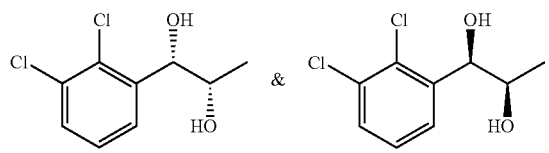

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~(m, 3H)

Preparation Example 60

Synthesis of 1-(2-fluorophenyl)-trans-1-propene

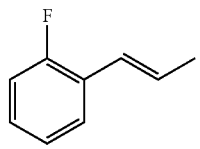

The substantially same method as described in Preparation Example 1 was conducted, except that 2-fluorobenzenealdehyde was used instead of 2-chlorobenzenealdehyde, to obtain the title compound (6.67 g, yield 61%).

$^1$H NMR (400 MHz, CDCl$_3$) δ1.94 (d, J=6.8 Hz, 3H), 6.30~6.38 (m, 1H), 6.57 (d, J=16 Hz, 1H), 7.00~7.41 (m, 4H)

Preparation Example 61

Synthesis of 1-(2-fluorophenyl)-(S,S)-1,2-propanediol

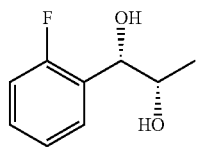

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 62

Synthesis of 1-(2-fluorophenyl)-(R,R)-1,2-propanediol

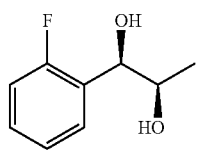

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 63

Synthesis of 2-iodobenzenealdehyde

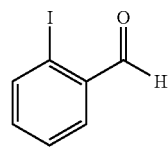

In a flask, 2-iodobenzyl alcohol (4 g, 17.09 mmol) was dissolved in dichloromethane (MC, 85 ml), and then, manganese oxide (MnO$_2$, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

$^1$H NMR (400 MHz, CDCl$_3$) δ7.30~7.99 (m, 4H), 10.10 (s, 1H)

Preparation Example 64

Synthesis of 1-(2-iodophenyl)-trans-1-propene

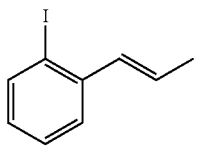

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR (400 MHz, CDCl$_3$) δ1.95 (dd, J=6.8 Hz, 1.6 Hz, 3H), 6.09~6.18 (m, 1H), 6.60 (dd, J=15.66 Hz, 1.8 Hz, 1H), 6.89~7.84 (m, 4H)

Preparation Example 65

Synthesis of 1-(2-iodophenyl)-trans-1-butene

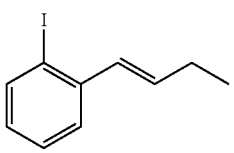

The substantially same method as described in Preparation Example 64 was conducted, except that 3-heptanone was used instead of 3-pentanone, to obtain the title compound (8.5 g, yield 75%).

$^1$H NMR (400 MHz, CDCl$_3$) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.89~7.85 (m, 4H)

Preparation Example 66

Synthesis of 1-(2-iodophenyl)-(S,S)-1,2-propanediol

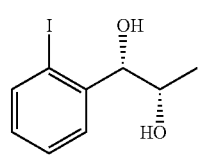

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR (400 MHz, CDCl$_3$) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01~7.87 (m, 4H)

Preparation Example 67

Synthesis of 1-(2-iodorophenyl)-(R,R)-1,2-propanediol

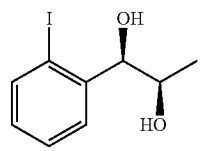

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR (400 MHz, CDCl$_3$) δ1.26 (d, J=6.4 Hz, 3H), 2.35 (br s, 1H), 2.85 (br d, J=4.0 Hz, 1H), 3.98 (t, J=6.2 Hz, 1H), 4.80 (dd, J=5.0, 4.4 Hz, 1H), 7.00~7.87 (m, 4H)

Preparation Example 68

Synthesis of 1-(2-iodophenyl)-(S,S)-1,2-butanediol

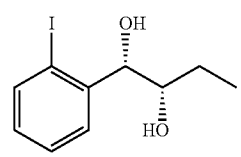

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 69

Preparation of 1-(2-chlorophenyl)-(S,S)-1,2-(Bis-trimethylsilanyloxy)propane

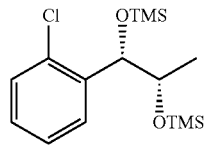

To a stirred solution of 1-(2-chlorophenyl)-(S,S)-1,2-propanediol (Preparation example 14, 67 g, 0.35 mol) in CH$_2$Cl$_2$ (670 ml) was added Et$_3$N (200 mL, 1.43 mol) and TMSCl (113.9 mL, 0.89 mol) at 0° C. under N$_2$. The reaction mixture was allowed to stir at 0° C. for 3 hr. The reaction mixture was quenched with H$_2$O (650 mL) at 0° C. The organic layer was separated and collected.

The aqueous layer was extracted with CH$_2$Cl$_2$ (300 mL), dried over MgSO$_4$. Concentration under vacuum provided a crude product. 104.18 g (117.44%).

$^1$H NMR (400 MHz, CDCl$_3$) δ-0.053 (s, 9H), 0.044 (s, 9H), 1.15 (d, J=5.6 Hz, 3H), 3.977~3.918 (m, 1H), 4.973 (d, J=6.4 Hz, 1H), 7.207~7.165 (m, 1H), 7.321~7.245 (m, 2H), 7.566~7.543 (m, 1H)

Preparation Example 70

Preparation of 1-(2-chlorophenyl)-(R,R)-1,2-(Bis-trimethylsilanyloxy)propane

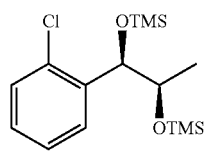

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).

¹H NMR (400 MHz, CDCl₃) δ-0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 71

Preparation of 1-(2-chlorophenyl)-1,2-(Bis-trimethylsilanyloxy)propane

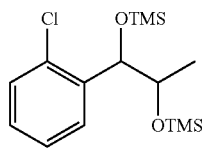

The substantially same method as described in Preparation Example 69 was conducted, except that 1-(2-chlorophenyl)propane-1,2-diol (Preparation example 16) was used instead of 1-(2-chlorophenyl)-(S,S)-1,2-propanediol (Preparation example 14) to obtain the title compound (5.2 g, yield 90~120%).
¹H NMR (400 MHz, CDCl₃) δ-0.053 (s, 9H), 0.044 (s, 9H), 1.15 (d, J=5.6 Hz, 3H), 3.977~3.918 (m, 1H), 4.973 (d, J 6.4 Hz, 1H), 7.21~7.54 (m, 4H)

Preparation Example 72

Preparation of 1-(2-chlorophenyl)-(S,R)-1,2-(Bis-trimethylsilanyloxy)propane

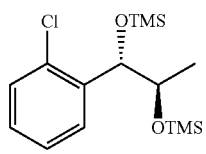

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).
¹H NMR (400 MHz, CDCl₃) δ-0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 73

Preparation of 1-(2-chlorophenyl)-(R,S)-1,2-(Bis-trimethylsilanyloxy)propane

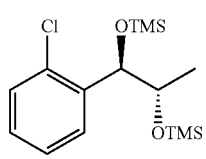

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).
¹H NMR (400 MHz, CDCl₃) δ-0.053 (s, 9H), 0.044 (s, 9H), 1.15 (d, J=5.6 Hz, 3H), 3.977~3.918 (m, 1H), 4.973 (d, J=6.4 Hz, 1H), 7.21~7.54 (m, 4H)

Preparation Example 74

Preparation of 1-(2-chlorophenyl)-(S,S)-1,2-(Bis-trimethylsilanyloxy)butane

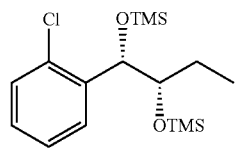

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).
¹H NMR (400 MHz, CDCl₃) δ-0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 75

Preparation of 1-(2-chlorophenyl)-(R,R)-1,2-(Bis-trimethylsilanyloxy)butane

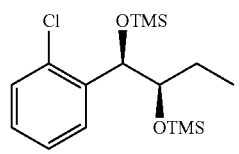

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).
¹H NMR (400 MHz, CDCl₃) δ-0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 76

Preparation of 1-(2-chlorophenyl)-1,2-(Bis-trimethylsilanyloxy)butane

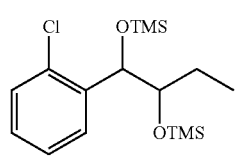

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).

$^1$H NMR (400 MHz, CDCl$_3$) δ-0.053 (s, 9H), 0.044 (s, 9H), 1.01 (t, J=7.4 Hz, 3H), 1.52~1.65 (m, 2H), 3.69~3.75 (m, 1H), 5.05 (t, J=5.0 Hz, 1H), 7.23~7.54 (m, 4H)

Preparation Example 77

Preparation of 1-(2-chlorophenyl)-3-methyl-(S,S)-1,2-(Bis-trimethylsilanyloxy)-butane

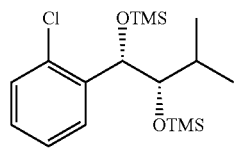

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title (2.7 g, yield 90~120%). $^1$H NMR (400 MHz, CDCl$_3$) δ-0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 78

Preparation of 1-(2-chlorophenyl)-3-methyl-(R,R)-1,2-(Bis-trimethylsilanyloxy)-butane

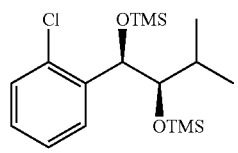

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).

$^1$H NMR (400 MHz, CDCl$_3$) δ-0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 79

Preparation of 1-(2-chlorophenyl)-3-methyl-1,2-(Bis-trimethylsilanyloxy)-butane

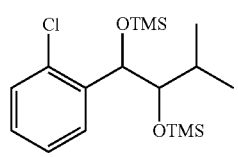

The substantially same method as described in Preparation Example 69 was conducted, except that 1-(2-chlorophenyl)-3-methyl-1,2-butanediol (Preparation example 22) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ-0.053 (s, 9H), 0.044 (s, 9H), 1.07 (t, J=7.2 Hz, 6H), 1.83~1.89 (m, 1H), 3.53~3.56 (m, 1H), 5.22~5.25 (m, 1H), 7.23~7.55 (m, 4H)

Preparation Example 80

Preparation of 1-(2-chlorophenyl)-(S,S)-1,2-(Bis-trimethylsilanyloxy)-hexane

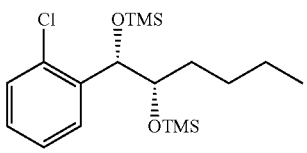

The substantially same method as described in Preparation Example 69 was conducted, except that 1-(2-chlorophenyl)-(S,S)-1,2-hexanediol (Preparation example 23) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ-0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 81

Preparation of 1-(2-chlorophenyl)-(S,S)-1,2-(Bis-trimethylsilanyloxy)-hexane

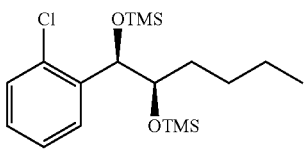

The substantially same method as described in Preparation Example 69 was conducted, except that 1-(2-chlorophenyl)-(R,R)-1,2-hexanediol (Preparation example 24) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ-0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 82

Preparation of 1-(2-chlorophenyl)-(S,S)-1,2-(Bis-trimethylsilanyloxy)-hexane

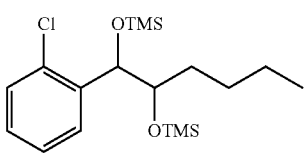

The substantially same method as described in Preparation Example 69 was conducted, except that 1-(2-chlorophenyl)-1,2-hexanediol (Preparation example 25) was used instead of 1-(2-chlorophenyl)-(S,S)-1,2-propanediol (Preparation example 14) to obtain the title compound (3.2 g, yield 90~120%).

$^1$H NMR (400 MHz, CDCl$_3$) δ -0.053 (s, 9H), 0.044 (s, 9H), 0.90 (t, J=7.2 Hz, 3H), 1.35~1.65 (m, 6H), 3.78~3.83 (m, 1H), 5.04 (t, J=5.0 Hz, 1H), 7.23~7.53 (m, 4H)

Preparation Example 83

Preparation of 1-(2,4-dichlorophenyl)-(S,S)-1,2-(Bis-trimethylsilanyloxy)-propane

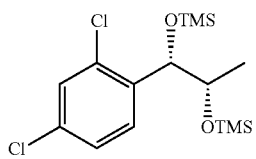

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90120%).

$^1$H NMR (400 MHz, CDCl$_3$) δ -0.053 (s, 9H), 0.044 (s, 9H), 1.22 (d, J=6.4 Hz, 3H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 84

Preparation of 1-(2,6-dichlorophenyl)-(S,S)-1,2-(Bis-trimethylsilanyloxy)-propane

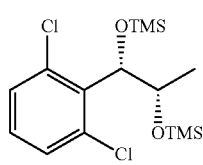

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).

$^1$H NMR (400 MHz, CDCl$_3$) δ -0.053 (s, 9H), 0.044 (s, 9H), 1.10 (d, J=6.4 Hz, 3H), 4.47~4.54 (m, 1H), 5.24 (t, J=8.8 Hz, 1H), 7.13~7.36 (m, 3H)

Preparation Example 85

Preparation of 1-(2,3-dichlorophenyl)-(S,S)-1,2-(Bis-trimethylsilanyloxy)-propane

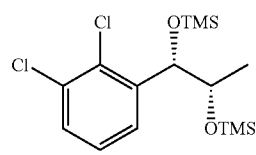

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).

$^1$H NMR (400 MHz, CDCl$_3$) δ -0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 86

Preparation of 1-(2,4-dichlorophenyl)-(S,S)-1,2-(Bis-trimethylsilanyloxy)-butane

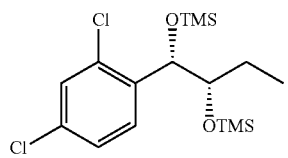

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ -0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 87

Preparation of 1-(2,6-dichlorophenyl)-(S,S)-1,2-(Bis-trimethylsilanyloxy)-butane

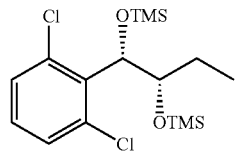

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ-0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 88

Preparation of 1-(2,4-dichlorophenyl)-3-methyl-(S,S)-1,2-(Bis-trimethylsilanyloxy)-butane

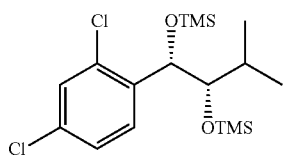

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).

$^1$H NMR (400 MHz, CDCl$_3$) δ-0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 89

Preparation of 1-(2,6-dichlorophenyl)-3-methyl-(S,S)-1,2-(Bis-trimethylsilanyloxy)-butane

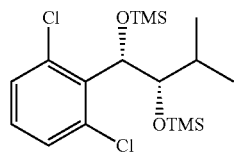

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ-0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 90

Preparation of 1-(2,4-dichlorophenyl)-(S,S)-1,2-(Bis-trimethylsilanyloxy)-hexane

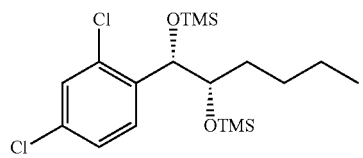

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

$^1$H NMR (400 MHz, CDCl$_3$) δ-0.053 (s, 9H), 0.044 (s, 9H), 0.89~0.93 (m, 3H), 1.30~1.39 (m, 2H), 1.49~1.52 (m, 2H), 1.56~1.6 (m, 2H), 3.72~3.77 (m, 1H), 4.98 (t, J=4.8 Hz, 1H), 7.28~7.50 (m, 3H)

Preparation Example 91

Preparation of 1-(2,6-dichlorophenyl)-(S,S)-1,2-(Bis-trimethylsilanyloxy)-hexane

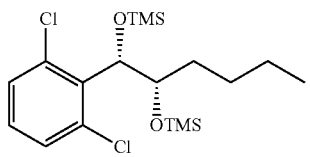

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

$^1$H NMR (400 MHz, CDCl$_3$) δ-0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 92

Preparation of 1-(2,4-dichlorophenyl)-(R,R)-1,2-(Bis-trimethylsilanyloxy)-propane

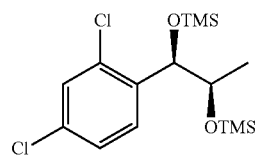

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

$^1$H NMR (400 MHz, CDCl$_3$) δ-0.053 (s, 9H), 0.044 (s, 9H), 1.22 (d, J=6.4 Hz, 3H), 3.90~3.95 (m, 1H), 4.94 (t, J=5.0 Hz, 1H), 7.31~7.49 (m, 3H)

Preparation Example 93

Preparation of 1-(2,6-dichlorophenyl)-(R,R)-1,2-(Bis-trimethylsilanyloxy)-propane

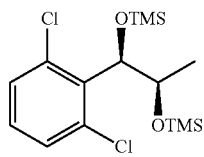

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ -0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.36 (m, 3H)

Preparation Example 94

Preparation of 1-(2,3-dichlorophenyl)-(R,R)-1,2-(Bis-trimethylsilanyloxy)-propane

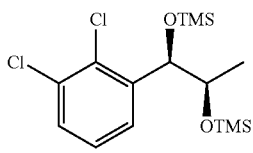

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

$^1$H NMR (400 MHz, CDCl$_3$) δ -0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 95

Preparation of 1-(2,4-dichlorophenyl)-(R,R)-1,2-(Bis-trimethylsilanyloxy)-butane

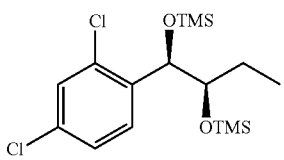

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

$^1$H NMR (400 MHz, CDCl$_3$) δ -0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 96

Preparation of 1-(2,6-dichlorophenyl)-(R,R)-1,2-(Bis-trimethylsilanyloxy)-butane

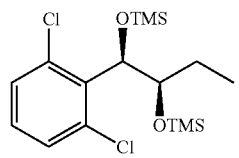

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ -0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 97

Preparation of 1-(2,4-dichlorophenyl)-3-methyl-(R,R)-1,2-(Bis-trimethylsilanyloxy)-butane

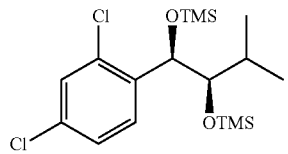

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).

$^1$H NMR (400 MHz, CDCl$_3$) δ -0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 98

Preparation of 1-(2,6-dichlorophenyl)-3-methyl-(R,R)-1,2-(Bis-trimethylsilanyloxy)-butane

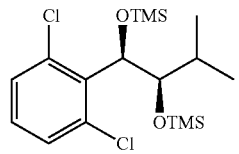

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-1,2-propanediol (Preparation example 14) to obtain the title compound (3.4 g, yield 90~120%).

$^1$H NMR (400 MHz, CDCl$_3$) δ -0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 99

Preparation of 1-(2,4-dichlorophenyl)-(R,R)-1,2-(Bis-trimethylsilanyloxy)-hexane

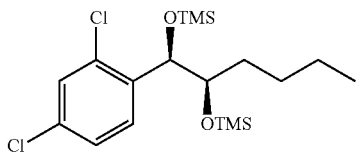

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).

$^1$H NMR (400 MHz, CDCl$_3$) δ -0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8 Hz, 1H), 7.28~7.50 (m, 3H)

Preparation Example 100

Preparation of 1-(2,6-dichlorophenyl)-(R,R)-1,2-(Bis-trimethylsilanyloxy)-hexane

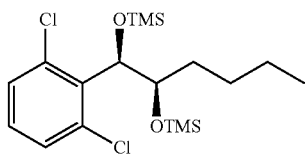

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).

$^1$H NMR (400 MHz, CDCl$_3$) δ -0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 101

Preparation of 1-(2,4-dichlorophenyl)-1,2-(Bis-trimethylsilanyloxy)-propane

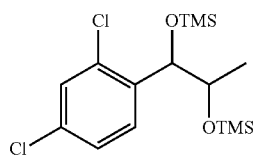

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ -0.053 (s, 9H), 0.044 (s, 9H), 1.22 (d, J=6.4 Hz, 3H), 3.90~3.95 (m, 1H), 4.94 (t, J=5.0 Hz, 1H), 7.31~7.49 (m, 3H)

Preparation Example 102

Preparation of 1-(2,6-dichlorophenyl)-1,2-(Bis-trimethylsilanyloxy)-propane

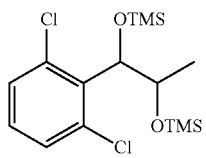

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ -0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.36 (m, 3H)

Preparation Example 103

Preparation of 1-(2,3-dichlorophenyl)-1,2-(Bis-trimethylsilanyloxy)-propane

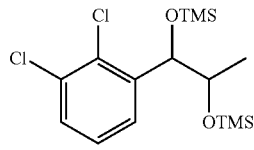

The substantially same method as described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90120%).

$^1$H NMR (400 MHz, CDCl$_3$) δ-0.053 (s, 9H), 0.044 (s, 9H), 1.10 (d, J=6.4 Hz, 3H), 4.47~4.54 (m, 1H), 5.24 (t, J=8.8 Hz, 1H), 7.18~7.22 (m, 3H)

Preparation Example 104

Preparation of 1-(2,4-dichlorophenyl)-1,2-(Bis-trimethylsilanyloxy)-butane

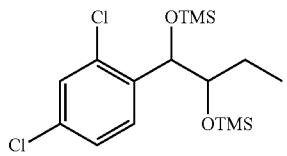

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).

$^1$H NMR (400 MHz, CDCl$_3$) δ-0.053 (s, 9H), 0.044 (s, 9H), 1.02 (t, J=7.4 Hz, 3H), 1.54~1.61 (m, 2H), 3.65~3.68 (m, 1H), 5.01 (t, J=5.0 Hz, 1H), 7.31~7.49 (m, 3H)

Preparation Example 105

Preparation of 1-(2,6-dichlorophenyl)-1,2-(Bis-trimethylsilanyloxy)-butane

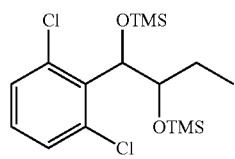

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).

$^1$H NMR (400 MHz, CDCl$_3$) δ-0.053 (s, 9H), 0.044 (s, 9H), 0.97 (t, J=7.6 Hz, 3H), 1.26~1.53 (m, 2H), 4.22~4.26 (m, 1H), 5.26 (t, J=8.4 Hz, 1H), 7.17~7.35 (m, 3H)

Preparation Example 106

Preparation of 1-(2,4-dichlorophenyl)-3-methyl-1,2-(Bis-trimethylsilanyloxy)-butane

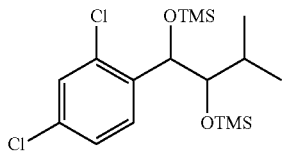

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~420%).

$^1$H NMR (400 MHz, CDCl$_3$) δ-0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.30~7.53 (m, 3H)

Preparation Example 107

Preparation of 1-(2,6-dichlorophenyl)-3-methyl-1,2-(Bis-trimethylsilanyloxy)-butane

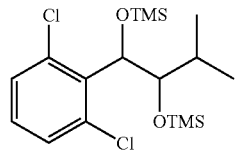

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).

$^1$H NMR (400 MHz, CDCl$_3$) δ-0.053 (s, 9H), 0.044 (s, 9H), 1.00 (d, J=6.8 Hz, 6H), 1.60~1.65 (m, 1H), 4.13~4.18 (m, 1H), 5.36 (t, J=7.6 Hz, 1H), 7.17~7.35 (m, 3H)

Preparation Example 108

Preparation of 1-(2,4-dichlorophenyl)-1,2-(Bis-trimethylsilanyloxy)-hexane

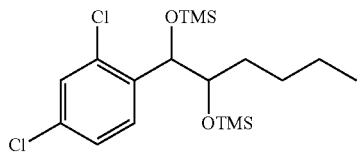

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).

¹H NMR (400 MHz, CDCl₃) δ -0.053 (s, 9H), 0.044 (s, 9H), 0.89~0.93 (m, 3H), 1.30~1.39 (m, 2H), 1.49~1.52 (m, 2H), 1.56~1.62 (m, 2H), 3.72~3.77 (m, 1H), 4.98 (t, J=4.8 Hz, 1H), 7.28~7.50 (m, 3H)

Preparation Example 109

Preparation of 1-(2,6-dichlorophenyl)-1,2-(Bis-trimethylsilanyloxy)-hexane

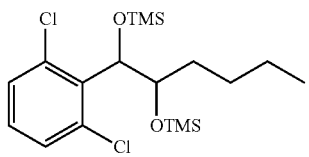

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).

¹H NMR (400 MHz, CDCl₃) δ -0.053 (s, 9H), 0.044 (s, 9H), 0.85 (t, J=6.7 Hz, 3H), 1.20~1.31 (m, 4H), 1.45~1.53 (m, 2H), 4.28~4.33 (m, 1H), 5.25 (t, J=8.4 Hz, 1H), 7.18~7.35 (m, 3H)

Preparation Example 110

Preparation of 1-(2-fluorophenyl)-(S,S)-1,2-(Bis-trimethylsilanyloxy)-propane

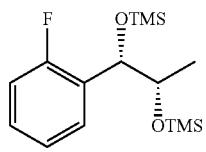

The substantially same method as described in Preparation Example 69 was conducted, except that 1-(2-fluorophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).

¹H NMR (400 MHz, CDCl₃) δ -0.053 (s, 9H), 0.044 (s, 9H), 1.15 (d, J=6.4 Hz, 3H), 3.90~3.98 (m, 1H), 4.78 (dd, J=4.4, 7.2 Hz, 1H), 7.04~7.50 (m, 4H)

Preparation Example 111

Preparation of 1-(2-fluorophenyl)-(R,R)-1,2-(Bis-trimethylsilanyloxy)-propane

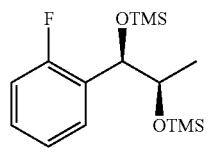

The substantially same method as described in Preparation Example 69 was conducted, except that 1-(2-fluorophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

¹H NMR (400 MHz, CDCl₃) δ -0.053 (s, 9H), 0.044 (s, 9H), 1.15 (d, J=6.4 Hz, 3H), 3.90~3.98 (m, 1H), 4.78 (dd, J=4.4, 7.2 Hz, 1H), 7.04~7.50 (m, 4H)

Preparation Example 112

Preparation of 1-(2-iodophenyl)-(S,S)-1,2-(Bis-trimethylsilanyloxy)-propane

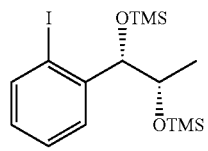

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%).

¹H NMR (400 MHz, CDCl₃) δ -0.053 (s, 9H), 0.044 (s, 9H), 1.27 (d, J=6.4 Hz, 3H), 3.99 (t, J=6.0 Hz, 1H), 4.81 (d, J=4.0 Hz, 1H), 7.01~7.87 (m, 4H)

Preparation Example 113

Preparation of 1-(2-iodophenyl)-(R,R)-1,2-(Bis-trimethylsilanyloxy)-propane

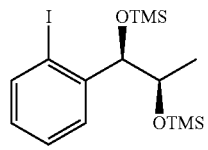

The substantially same method as described in Preparation Example 69 was conducted, except that 1-(2-iodophenyl)-(R, R)-1,2-propanediol (Preparation example 67) was used instead of 1-(2-chlorophenyl)-(S,S)-1,2-propanediol (Preparation example 14) to obtain the title compound (2.8 g, yield 90~120%).

$^{1}$H NMR (400 MHz, CDCl$_{3}$) δ-0.053 (s, 9H), 0.044 (s, 9H), 1.26 (d, J=6.4 Hz, 3H), 3.98 (t, J=6.2 Hz, 1H), 4.88 (d, J=4.4 Hz, 1H), 7.00~7.87 (m, 4H)

Preparation Example 114

Preparation of 1-(2-iodophenyl)-(S,S)-1,2-(Bis-trimethylsilanyloxy)-butane

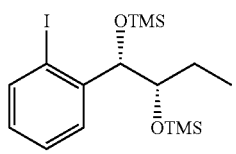

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).

$^{1}$H NMR (400 MHz, CDCl$_{3}$) δ-0.053 (s, 9H), 0.044 (s, 9H), 1.04 (t, J=7.6 Hz, 3H), 1.60~1.71 (m, 2H), 3.71~3.76 (m, 1H), 4.87 (d, J=4.8 Hz, 1H), 7.01~7.87 (m, 4H)

Preparation Example 115

Synthesis of 1-(2-chlorophenyl)-(R)-1-(methoxymethoxy)-propyl-(S)-2-carbamate

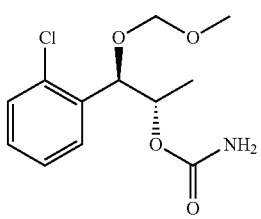 [SMILES: COCO[C@H](c1ccccc1Cl)[C@H](C)OC(N)=O]

1-(2-chlorophenyl)-(S)-1-methoxymethoxy-(S)-2-hydroxypropyl (0.80 g) obtained in Preparation Example 54, tetrahydrofuran (THF, 10 ml), and carbonyldiimidazole (CDI, 0.85 g) were put into a flask and stirred at the room temperature. After approximately 3 hours, ammonia solution (NH$_{4}$OH, 0.8 ml) was added thereto. When the reaction was completed, the obtained product was washed with 1M HCl solution and ethylacetate (EA). The separated organic layer was dehydrated with anhydrous magnesium sulfate (MgSO$_{4}$), filtrated, and concentrated under reduced pressure. The concentrated residue was purified by a silica gel column chromatography, to obtain the title compound (0.49 g, yield 30~60%).

$^{1}$H NMR (400 MHz, CDCl$_{3}$) δ1.28 (d, J=6.4 Hz, 3H), 3.40 (s, 3H), 4.58 (dd, J=6.8, J=40.8 Hz 2H), 4.62 (br s, 2H), 5.15~5.20 (m, 2H), 7.25~7.53 (m, 4H)

Example 1

Preparation of 1-(2-chlorophenyl)-(S)-1-hydroxypropyl-(S)-2-carbamate(1)

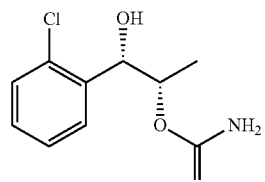

To a stirred solution of crude 1-(2-chlorophenyl)-(S,S)-1,2-(Bis-trimethylsilanyloxy)propane (preparation example 69, 104 g, 0.31 mol) in toluene (670 mL) was added by chlorosulfonyl isocyanate (62.5 mL, 0.71 mol) at 0° C. The reaction mixture was stirred for 2 hr. The reaction mixture was quenched with ice water and then was stirred by additional cold H$_{2}$O (500 mL) for 2 hr. After separation of organic layer, the aqueous was adjusted pH2~3 with sat. NaHCO$_{3}$ (400 mL) and extracted with EtOAc (300 mL×3). The EtOAc layer was washed with sat. NaHCO$_{3}$ (500 mL) and H$_{2}$O (500 mL). The organic phase was treated with Charcol for 1.5 hr. The organic phase was filtered with Cellite, dried over MgSO$_{4}$. Filterion and concentration under vacuum provided the title compound of white solid (yield 85% (71.1 g), ee=99.9% MP=83~84° C., [α]$_{D}$=+57.8 (c=0.25, MeOH))

$^{1}$H NMR (400 MHz, CDCl$_{3}$) δ1.24 (d, J=6.4 Hz, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

$^{13}$C NMR (100 MHz, CDCl$_{3}$) δ16.4, 73.1, 75.0, 127.0, 128.4, 129.1, 129.5, 132.7, 138.0, 156.6

Example 2

Preparation of 1-(2-chlorophenyl)-(R)-1-hydroxypropyl-(R)-2-carbamate(2)

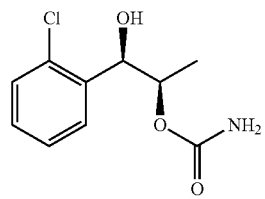

The substantially same method as described in Example 1 was conducted, except that 1-(2-chlorophenyl)-(R,R)-1,2-(Bis-trimethylsilanyloxy)propane (Preparation example 70) was used instead of 1-(2-chlorophenyl)-(S,S)-1,2-(Bis-trimethylsilanyloxy)propane (Preparation example 69) to obtain the title compound (5.7 g, yield 60~90%).

¹H NMR (400 MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 3

Preparation of 1-(2-chlorophenyl)-1-hydroxypropyl-2-carbamate(3)

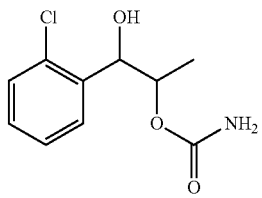

The substantially same method as described in Example 1 was conducted, except that 1-(2-chlorophenyl)-1,2-(Bis-trimethylsilanyloxy)propane (Preparation example 71) was used instead of 1-(2-chlorophenyl)-(S,S)-1,2-(Bis-trimethylsilanyloxy)propane (Preparation example 69) to obtain the title compound (3.8 g, yield 60~90%).
¹H NMR (400 MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 4

Preparation of 1-(2-chlorophenyl)-(S)-1-hydroxypropyl-(R)-2-carbamate(4)

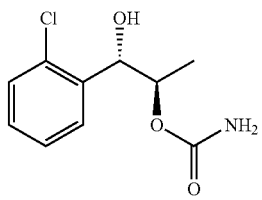

The substantially same method as described in Example 1 was conducted, except that 1-(2-chlorophenyl)-(S,R)-1,2-(Bis-trimethylsilanyloxy)propane (Preparation example 72) was used instead of 1-(2-chlorophenyl)-(S,S)-1,2-(Bis-trimethylsilanyloxy)propane (Preparation example 69) to obtain the title compound (2.4 g, yield 60~90%).
¹H NMR (400 MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6, J=7.8, 1H)

Example 5

Preparation of 1-(2-chlorophenyl)-(R)-1-hydroxypropyl-(S)-2-carbamate(5)

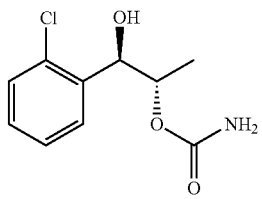

The substantially same method as described in Example 1 was conducted, except that 1-(2-chlorophenyl)-(R,S)-1,2-(Bis-trimethylsilanyloxy)propane (Preparation example 73) was used instead of 1-(2-chlorophenyl)-(S,S)-1,2-(Bis-trimethylsilanyloxy)propane (Preparation example 69) to obtain the title compound (2.3 g, yield 60~90%).
¹H NMR (400 MHz, CDCl₃) δ1.24 (d, J=6.4, 3H), 2.91 (d, J=4.8, 1H), 4.68 (br s, 2H), 5.06~5.09 (m, 1H), 5.18~5.21 (m, 1H), 7.23~7.39 (m, 3H), 7.55 (dd, J=1.6 Hz, J=7.8 Hz, 1H)

Example 6

Preparation of 1-(2-chlorophenyl)-(S)-1-hydroxybutyl-(S)-2-carbamate(6)

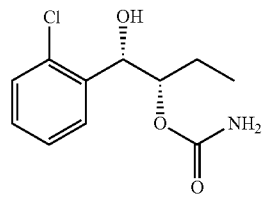 [SMILES: CC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy)propane (Preparation example 69) to obtain the title compound (2.6 g, yield 60~90%).
¹H NMR (400 MHz, CDCl₃) δ0.96 (t, J=7.4 Hz, 3H), 1.57~1.73 (m, 2H), 3.01 (d, J=5.6 Hz, 1H), 4.74 (br s, 2H), 4.95 (dt, J=7.2, 8.8 Hz, 1H), 5.23 (t, J=5.6 Hz, 1H), 7.22~7.54 (m, 4H)

Example 7

Synthesis of 1-(2-chlorophenyl)-(R)-1-hydroxybutyl-(R)-2-carbamate(7)

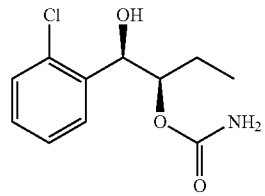 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR (400 MHz, CDCl$_3$) δ0.94 (t, J=7.4 Hz, 3H), 1.53~1.73 (m, 2H), 2.92 (s, 1H), 4.78 (br s, 2H), 4.91~4.96 (m, 1H), 5.22 (d, J=5.5 Hz, 1H), 7.20~7.54 (m, 4H)

Example 8

Synthesis of 1-(2-chlorophenyl)-1-hydroxybutyl-2-carbamate(8)

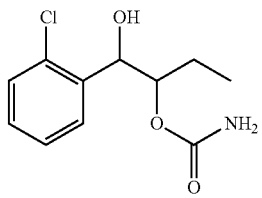 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR (400 MHz, CDCl$_3$) δ0.97 (t, J=7 Hz, 3H), 1.58~1.74 (m, 2H), 2.94 (d, J=6 Hz, 1H), 4.69 (br s, 2H), 4.94~4.99 (m, 1H), 5.24 (t, J=6 Hz, 1H), 7.23~7.56 (m, 4H)

Example 9

Synthesis of 1-(2-chlorophenyl)-(S)-1-hydroxy-3-methyl-butyl-(S)-2-carbamate(9)

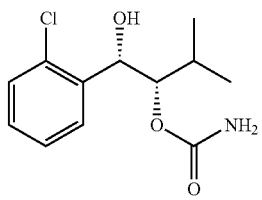 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.01 (d, J=6.4 Hz, 3H), 1.09 (d, J=6.8 Hz, 3H), 2.06 (m, 1H), 2.75 (d, J=6.8 Hz, 1H), 4.58 (br s, 2H), 4.85~4.88 (m, 1H), 5.34~5.37 (m, 1H), 7.22~7.33 (m, 2H), 7.35~7.37 (m, 1H), 7.51~7.53 (m, 1H)

Example 10

Synthesis of 1-(2-chlorophenyl)-(R)-1-hydroxy-3-methyl-butyl-(R)-2-carbamate(10)

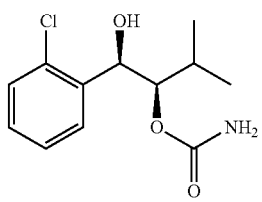 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR (400 MHz, CDCl$_3$) δ1.01 (d, J=6.8 Hz, 3H), 1.09 (d, J=6.8 Hz, 3H), 2.06 (m, 1H), 2.73 (d, J=6.8 Hz, 1H), 4.57 (br s, 2H), 4.85~4.88 (m, 1H), 5.34~5.37 (m, 1H), 7.24~7.30 (m, 2H), 7.35~7.37 (m, 1H), 7.51~7.53 (m, 1H)

Example 11

Synthesis of 1-(2-chlorophenyl)-1-hydroxy-3-methyl-butyl-2-carbamate(11)

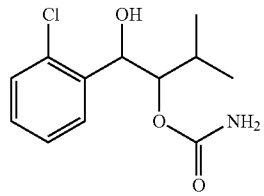 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.00 (d, J=6.4 Hz, 3H), 1.09 (d, J=6.4 Hz, 3H), 2.08 (m, 1H), 2.76 (d, J=6.0 Hz, 1H), 4.59 (br s, 2H), 4.87 (dd, J=7.2 Hz, 4.4 Hz, 1H), 5.36 (t, J=4.6, 1H), 7.23~7.54 (m, 4H)

Example 12

Synthesis of 1-(2-chlorophenyl)-(S)-1-hydroxyhexyl-(S)-2-carbamate(12)

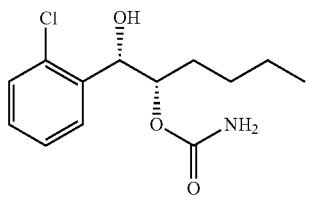 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR (400 MHz, CDCl$_3$) δ0.88 (t, J=7 Hz, 3H), 1.33~1.42 (m, 4H), 1.53~1.71 (m, 2H), 2.89 (d, J=5.6 Hz, 1H) 4.64 (br s, 2H), 5.04 (dt, J=5.0, 9.0 Hz, 1H), 5.20 (t, J=5.6 Hz, 1H), 7.23~7.55 (m, 4H)

Example 13

Synthesis of 1-(2-chlorophenyl)-(R)-1-hydroxy-hexyl-(R)-2-carbamate(13)

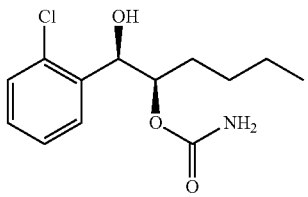 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy)propane (Preparation example 69) to obtain the title compound (2.2 g, yield 60~90%).

$^1$H NMR (400 MHz, CDCl$_3$) δ 0.89 (dd, J=5 Hz, 3H), 1.28~1.43 (m, 4H), 1.52~1.58 (m, 1H), 1.65~4.72 (m, 1H), 2.90 (d, J=6 Hz, 1H), 4.64 (br s, 2H), 5.01~5.06 (m, 1H), 5.22 (t, J=6 Hz, 1H), 7.22~7.56 (m, 4H)

Example 14

Synthesis of 1-(2-chlorophenyl)-1-hydroxyhexyl-2-carbamate(14)

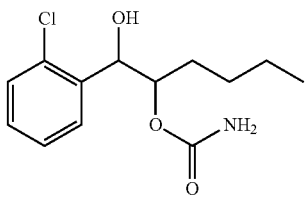 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy)propane (Preparation example 69) to obtain the title compound (2.1 g, yield 60~90%).

$^1$H NMR (400 MHz, CDCl$_3$) δ 0.88 (dd, J=5 Hz, 3H), 1.31~1.43 (m, 4H), 1.63~1.70 (m, 1H), 1.52~1.60 (m, 1H), 3.06 (d, J=6 Hz, 1H), 4.75 (br s, 2H), 5.00~5.05 (m, 1H), 5.21 (t, J=6 Hz, 1H), 7.22~7.55 (m, 4H)

Example 15

Synthesis of 1-(2,4-dichlorophenyl)-(S)-1-hydroxypropyl-(S)-2-carbamate(15)

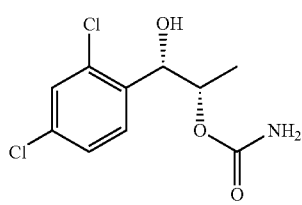 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)propane (Preparation Example 83) was used instead of 1-(2-chlorophenyl)-(S,S)-1,2-(Bis-trimethylsilanyloxy)propane (Preparation example 69) to obtain the title compound (1.8 g, yield 60~90%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 16

Synthesis of 1-(2,6-dichlorophenyl)-(S)-1-hydroxypropyl-(S)-2-carbamate(16)

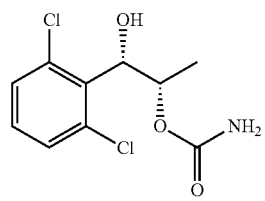 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)propane (Preparation Example 84) was used instead of 1-(2-chlorophenyl)-(S,S)-1,2-(Bis-trimethylsilanyloxy)propane (Preparation example 69) to obtain the title compound (2.6 g, yield 60~90%)

Example 17

Synthesis of 1-(2,3-dichlorophenyl)-(S)-1-hydroxypropyl-(S)-2-carbamate(17)

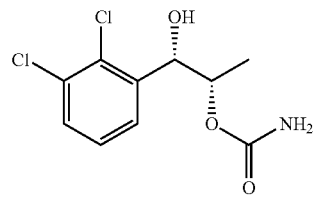 [SMILES: C[C@H](OC(N)=O)[C@@H](O)c1cccc(Cl)c1Cl]

The substantially same method as described in Example 1 was conducted, except that 1-(2,3-dichlorophenyl)-(S,S)-1,2-(Bis-trimethylsilanyloxy)propane (Preparation Example 85) was used instead of 1-(2-chlorophenyl)-(S,S)-1,2-(Bis-trimethylsilanyloxy)propane (Preparation example 69) to obtain the title compound (1.4 g, yield 60~90%)

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 18

Synthesis of 1-(2,4-dichlorophenyl)-(S)-1-hydroxy-butyl-(S)-2-carbamate(18)

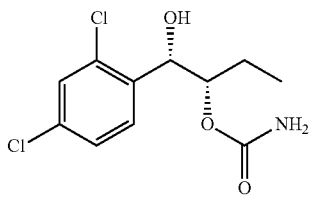 [SMILES: CC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)butane (Preparation Example 86) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 19

Synthesis of 1-(2,6-dichlorophenyl)-(S)-1-hydroxy-butyl-(S)-2-carbamate(19)

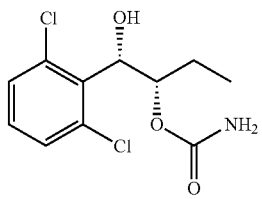

The substantially same method as described in Example 1 was conducted, except that 1-(2,6-dichlorophenyl)-(S,S)-1,2-(Bis-trimethylsilanyloxy)butane (Preparation Example 87) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 20

Synthesis of 1-(2,4-dichlorophenyl)-(S)-1-hydroxy-3-methyl-butyl-(S)-2-carbamate(20)

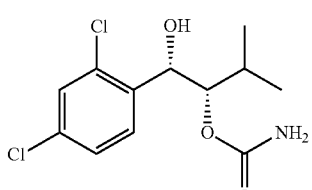

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 21

Synthesis of 1-(2,6-dichlorophenyl)-(S)-1-hydroxy-3-methyl-butyl-(S)-2-carbamate(21)

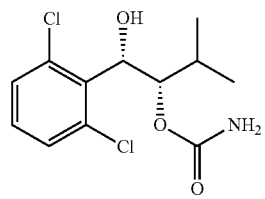 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 22

Synthesis of 1-(2,4-dichlorophenyl)-(S)-1-hydroxy-hexyl-(S)-2-carbamate(22)

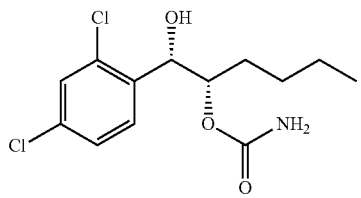

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy)propane (Preparation example 69) to obtain the title compound (2.2 g, yield 60~90%).

$^1$H NMR (400 MHz, CDCl$_3$) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m 3H)

Example 23

Synthesis of 1-(2,6-dichlorophenyl)-(S)-1-hydroxy-hexyl-(S)-2-carbamate(23)

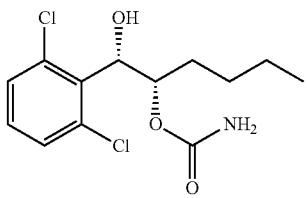 [SMILES: CCCC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy)propane (Preparation example 69) to obtain the title compound (2.1 g, yield 60~90%)

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 24

Synthesis of 1-(2,4-dichlorophenyl)-(R)-1-hydroxypropyl-(R)-2-carbamate(24)

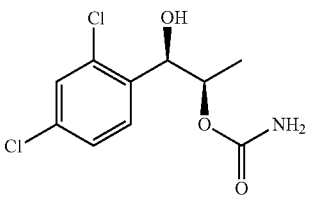 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy)propane (Preparation example 69) to obtain the title compound (1.2 g, yield 60~90%), $^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 25

Synthesis of 1-(2,6-dichlorophenyl)-(R)-1-hydroxypropyl-(R)-2-carbamate(25)

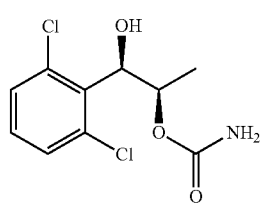 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy)propane (Preparation example 69) to obtain the title compound (1.7 g, yield 60~90%), $^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 26

Synthesis of 1-(2,3-dichlorophenyl)-(R)-1-hydroxypropyl-(R)-2-carbamate(26)

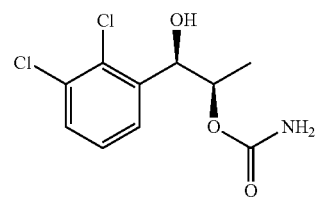 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy)propane (Preparation example 69) to obtain the title compound (2.0 g, yield 60~90%)

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 27

Synthesis of 1-(2,4-dichlorophenyl)-(R)-1-hydroxybutyl-(R)-2-carbamate(27)

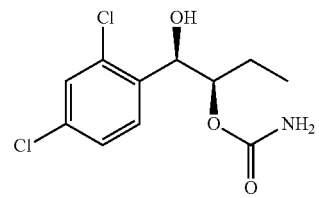 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 28

Synthesis of 1-(2,6-dichlorophenyl)-(R)-1-hydroxy-butyl-(R)-2-carbamate(28)

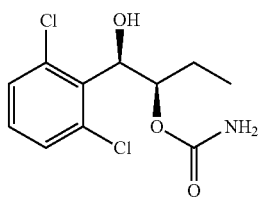 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 29

Synthesis of 1-(2,4-dichlorophenyl)-(R)-1-hydroxy-3-methyl-butyl-(R)-2-carbamate(29)

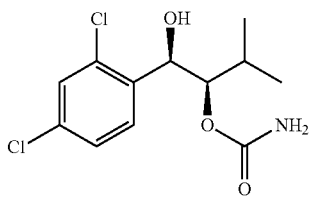 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-(S,S)-1,2-(Bis-trimethylsilanyloxy)propane (Preparation example 69) to obtain the title compound (2.8 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 30

Synthesis of 1-(2,6-dichlorophenyl)-(R)-1-hydroxy-3-methyl-butyl-(R)-2-carbamate(30)

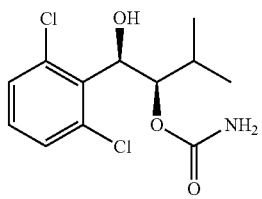 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy)propane (Preparation example 69) to obtain the title compound (2.6 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 31

Synthesis of 1-(2,4-dichlorophenyl)-(R)-1-hydroxy-hexyl-(R)-2-carbamate(31)

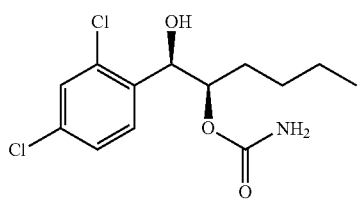 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR (400 MHz, CDCl$_3$) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Example 32

Synthesis of 1-(2,6-dichlorophenyl)-(R)-1-hydroxy-hexyl-(R)-2-carbamate(32)

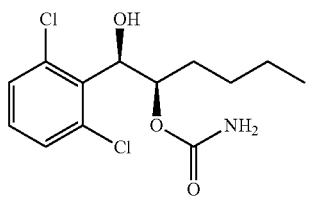 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 33

Synthesis of 1-(2,4-dichlorophenyl)-1-hydroxypropyl-2-carbamate(33)

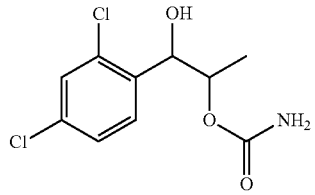 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Example 34

Synthesis of 1-(2,6-dichlorophenyl)-1-hydroxypropyl-2-carbamate(34)

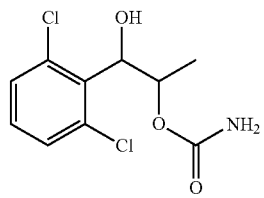 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 35

Synthesis of 1-(2,3-dichlorophenyl)-1-hydroxypropyl-2-carbamate(35)

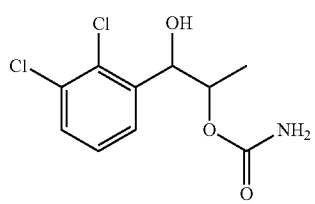 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Example 36

Synthesis of 1-(2,4-dichlorophenyl)-1-hydroxybutyl-2-carbamate(36)

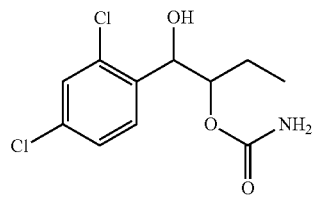 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Example 37

Synthesis of 1-(2,6-dichlorophenyl)-1-hydroxybutyl-2-carbamate(37)

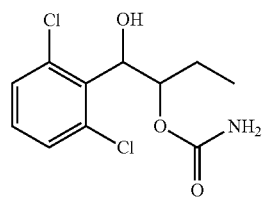 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Example 38

Synthesis of 1-(2,4-dichlorophenyl)-1-hydroxy-3-methyl-butyl-2-carbamate(38)

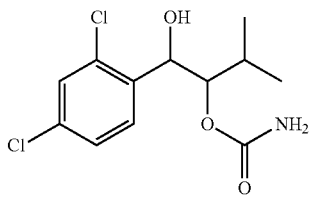 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Example 39

Synthesis of 1-(2,6-dichlorophenyl)-1-hydroxy-3-methyl-butyl-2-carbamate(39)

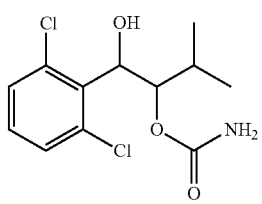 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Example 40

Synthesis of 1-(2,4-dichlorophenyl)-1-hydroxyhexyl-2-carbamate(40)

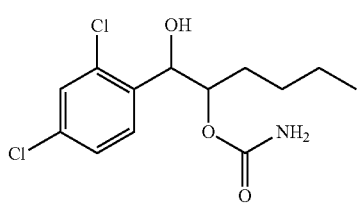 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy)propane (Preparation example 69) to obtain the title compound (2.6 g, yield 60~90%).

$^1$H NMR (400 MHz, CDCl$_3$) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Example 41

Synthesis of 1-(2,6-dichlorophenyl)-1-hydroxyhexyl-2-carbamate(41)

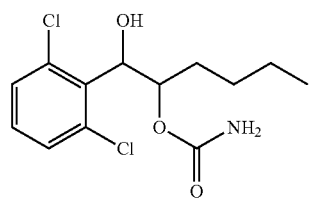 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Example 42

Synthesis of 1-(2-fluorophenyl)-(S)-1-hydroxypropyl-(S)-2-carbamate(42)

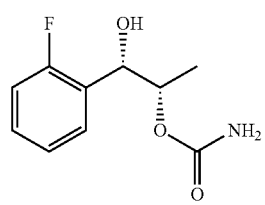

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy)propane (Preparation example 69) to obtain the title compound (1.8 g, yield 60~90%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Example 43

Synthesis of 1-(2-fluorophenyl)-(R)-1-hydroxypropyl-(R)-2-carbamate(43)

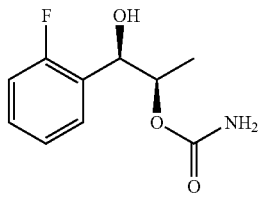

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Example 44

Synthesis of 1-(2-iodophenyl)-(S)-1-hydroxypropyl-(S)-2-carbamate(44)

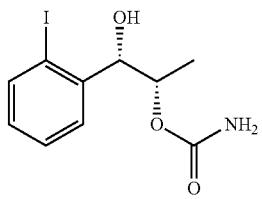

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy)propane (Preparation example 69) to obtain the title compound (2.2 g, yield 60~90%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Example 45

Synthesis of 1-(2-iodophenyl)-(R)-1-hydroxypropyl-(R)-2-carbamate(45)

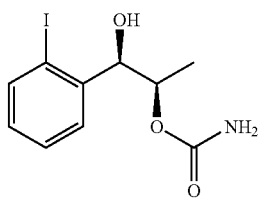

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR (400 MHz, CDCl$_3$) δ1.27 (d, J=6.4 Hz, 3H), 2.95 (d, J=3.6 Hz, 1H), 4.73 (br s, 2H), 5.01~5.11 (m, 2H), 7.01~7.86 (m, 4H)

Example 46

Synthesis of 1-(2-iodophenyl)-(S)-1-hydroxybutyl-(S)-2-carbamate(46)

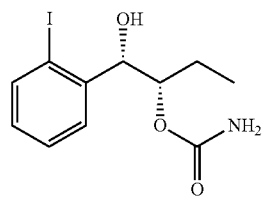 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy)propane (Preparation example 69) to obtain the title compound (2.1 g, yield 60~90%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Example 47

Preparation of 1-(2-chlorophenyl)-(R)-1-hydroxypropyl-(S)-2-carbamate(5)

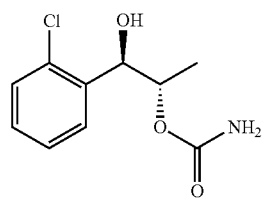

The substantially same method as described in Preparation Example 55 was conducted, except that 1-(2-chlorophenyl)-(R)-1-(methoxymethoxy)-propyl-(S)-2-carbamate (Preparation example 115) was used instead of 1-(2-chlorophenyl)-(R)-1-(methoxymethoxy)-(S)-2-propanol (Preparation example 55) to obtain the title compound (0.38 g, yield 50~80%).

¹H NMR (400 MHz, CDCl₃) δ1.24 (d, J=6.4, 3H), 2.91 (d, J=4.8 Hz, 1H), 4.68 (br s, 2H), 5.06~5.09 (m, 1H), 5.18~5.21 (m, 1H), 7.23~7.39 (m, 3H), 7.55 (dd, J=1.6 Hz, J=7.8 Hz, 1H)

Compounds 1 to 46 produced in Examples 1 to 46 are summarized in following Tables 1:

TABLES 1

| No. | X | n (position) | 1ˢᵗ Chiral | 2ⁿᵈ Chiral | R¹ |
|---|---|---|---|---|---|
| 1 | Cl | 1(2-) | S | S | Me |
| 2 | Cl | 1(2-) | R | R | Me |
| 3 | Cl | 1(2-) | Rac. | Rac. | Me |
| 4 | Cl | 1(2-) | S | R | Me |
| 5 | Cl | 1(2-) | R | S | Me |
| 6 | Cl | 1(2-) | S | S | Et |
| 7 | Cl | 1(2-) | R | R | Et |
| 8 | Cl | 1(2-) | Rac. | Rac. | Et |
| 9 | Cl | 1(2-) | S | S | Isopropyl |
| 10 | Cl | 1(2-) | R | R | Isopropyl |
| 11 | Cl | 1(2-) | Rac. | Rac. | Isopropyl |
| 12 | Cl | 1(2-) | S | S | butyl |
| 13 | Cl | 1(2-) | R | R | butyl |
| 14 | Cl | 1(2-) | Rac. | Rac. | butyl |
| 15 | Cl | 2(2,4-) | S | S | Me |
| 16 | Cl | 2(2,6-) | S | S | Me |
| 17 | Cl | 2(2,3-) | S | S | Me |
| 18 | Cl | 2(2,4-) | S | S | Et |
| 19 | Cl | 2(2,6-) | S | S | Et |
| 20 | Cl | 2(2,4-) | S | S | Isopropyl |
| 21 | Cl | 2(2,6-) | S | S | Isopropyl |
| 22 | Cl | 2(2,4-) | S | S | butyl |
| 23 | Cl | 2(2,6-) | S | S | butyl |
| 24 | Cl | 2(2,4-) | R | R | Me |
| 25 | Cl | 2(2,6-) | R | R | Me |
| 26 | Cl | 2(2,3-) | R | R | Me |
| 27 | Cl | 2(2,4-) | R | R | Et |
| 28 | Cl | 2(2,6-) | R | R | Et |
| 29 | Cl | 2(2,4-) | R | R | Isopropyl |
| 30 | Cl | 2(2,6-) | R | R | Isopropyl |
| 31 | Cl | 2(2,4-) | R | R | butyl |
| 32 | Cl | 2(2,6-) | R | R | butyl |
| 33 | Cl | 2(2,4-) | Rac. | Rac. | Me |
| 34 | Cl | 2(2,6-) | Rac. | Rac. | Me |
| 35 | Cl | 2(2,3-) | Rac. | Rac. | Me |
| 36 | Cl | 2(2,4-) | Rac. | Rac. | Et |
| 37 | Cl | 2(2,6-) | Rac. | Rac. | Et |
| 38 | Cl | 2(2,4-) | Rac. | Rac. | Isopropyl |
| 39 | Cl | 2(2,6-) | Rac. | Rac. | Isopropyl |
| 40 | Cl | 2(2,4-) | Rac. | Rac. | butyl |
| 41 | Cl | 2(2,6-) | Rac. | Rac. | butyl |
| 42 | F | 1(2-) | S | S | Me |
| 43 | F | 1(2-) | R | R | Me |
| 44 | I | 1(2-) | S | S | Me |
| 45 | I | 1(2-) | R | R | Me |
| 46 | I | 1(2-) | S | S | Et |

What is claimed is:

1. A process of the preparation of a compound of Chemical Formula 1, comprising the step of performing a carbamation of a compound of Chemical Formula 6 by reacting the compound of Chemical Formula 6 with chlorosulfonyl isocyanate, to produce a phenyl carbamate compound of Chemical Formula 1:

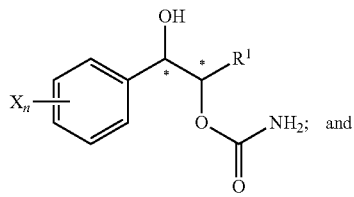

(Chemical Formula 1)

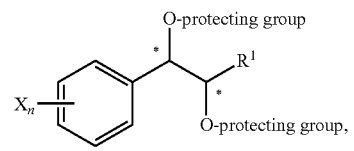

(Chemical Formula 6)

wherein X is one or more independently selected from halogens, n is an integer from 1 to 5, and R¹ is selected from the group consisting of a linear or branched alkyl group having 1-10 carbon atoms.

2. The process according to claim 1, which further comprises the step of protecting a diol compound of Chemical Formula 5 by introducing a protecting group into the diol compound, to produce the compound of Chemical Formula 6, prior to the carbamation step:

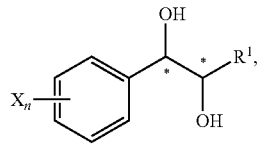

(Chemical Formula 5)

wherein X is one or more independently selected from halogens, n is an integer from 1 to 5, and R¹ is selected from the group consisting of a linear or branched alkyl group having 1-10 carbon atoms.

3. The process according to claim 2, which further comprises the step of performing dihydroxylation of a trans olefin compound of Chemical Formula 4, to produce the diol compound of Chemical Formula 5, prior to the protection step:

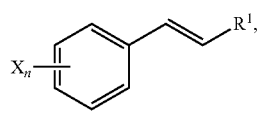

(Chemical Formula 4)

wherein X is one or more independently selected from halogens, n is an integer from 1 to 5, and R¹ is selected from the group consisting of a linear or branched alkyl group having 1-10 carbon atoms.

4. The process according to claim 3, which further comprises the step of producing the trans olefin compound of Chemical Formula 4 by reacting a compound of Chemical Formula 2 and a compound of Chemical Formula 3:

(Chemical Formula 2)

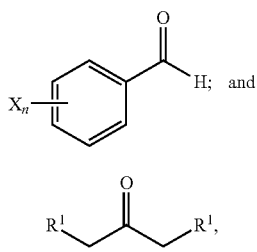

(Chemical Formula 3)

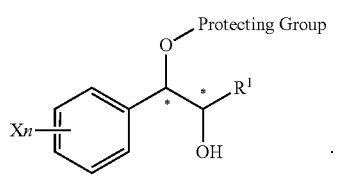

wherein X is one or more independently selected from halogens, n is an integer from 1 to 5, and $R^1$ is selected from the group consisting of a linear or branched alkyl group having 1-10 carbon atoms.

5. The method according to claim 3, wherein the dihydroxylation is performed using an asymmetric dihydroxylation catalyst.

6. The process according to claim 2, which further comprises the step of deprotecting a protected alcohol compound of Chemical Formula 8, to produce the diol compound of Chemical Formula 5, prior to the protection step:

(Chemical Formula 8)

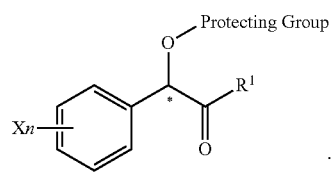

7. The process according to claim 6, which further comprises the step of reducing a compound of Chemical Formula 7, to produce the protected alcohol compound of Chemical Formula 8, prior to the deprotection step:

(Chemical Formula 7)

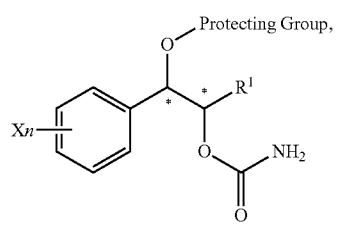

8. A process of the preparation of a compound of Chemical Formula 1, comprising the step of deprotecting a protected carbamate compound of Chemical Formula 9, to produce a phenyl carbamate compound of Chemical Formula 1:

(Chemical Formula 9)

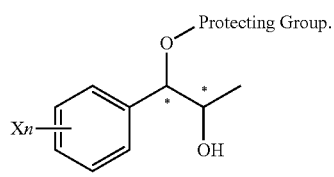

wherein X is one or more independently selected from halogens, n is an integer from 1 to 5, and $R^1$ is selected from the group consisting of a linear or branched alkyl group having 1-10 carbon atoms.

9. The process according to claim 8, which further comprises the step of performing a carbamation of a protected alcohol compound of Chemical Formula 8, to produce the protected carbamate compound of Chemical Formula 9, prior to the deperotecting step:

(Chemical Formula 8)

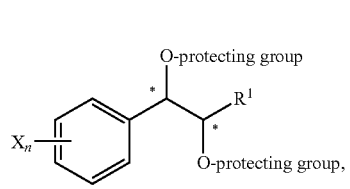

10. A compound represented by Chemical Formula 6:

(Chemical Formula 6)

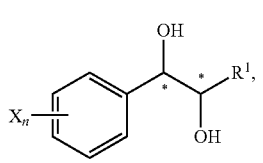

wherein X is one or more independently selected from halogens, n is an integer from 1 to 5, and $R^1$ is selected from the group consisting of a linear or branched alkyl group having 1-10 carbon atoms, and the protecting group is an alcohol-protecting group selected from the group consisting of trialkyl silyl group, ether group, and benzoyl group.

11. A process of the preparation of a compound of Chemical Formula 6, comprising the step of protecting a diol compound of Chemical Formula 5 by introducing a protecting group into the diol compound, to produce the compound of Chemical Formula 6:

(Chemical Formula 5)

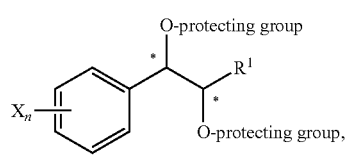

(Chemical Formula 6)

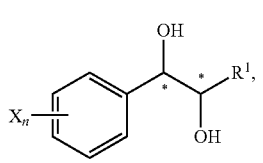

wherein X is one or more independently selected from halogens, n is an integer from 1 to 5, and $R^1$ is selected from the group consisting of a linear or branched alkyl group having 1-10 carbon atoms.

12. A compound represented by Chemical Formula 7:

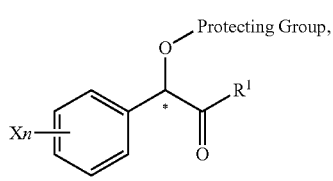

(Chemical Formula 7)

wherein X is one or more independently selected from halogens, n is an integer from 1 to 5, and $R^1$ is selected from the group consisting of a linear or branched alkyl group having 1-10 carbon atoms, and the protecting group is an alcohol-protecting group selected from the group consisting of trialkyl silyl group, ether group, and benzoyl group.

13. A compound represented by Chemical Formula 8:

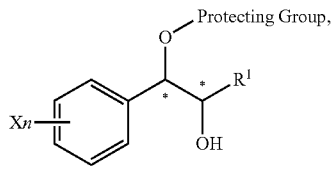

(Chemical Formula 8)

wherein X is one or more independently selected from halogens, n is an integer from 1 to 5, and $R^1$ is selected from the group consisting of a linear or branched alkyl group having 1-10 carbon atoms, and the protecting group is an alcohol-protecting group selected from the group consisting of trialkyl silyl group, ether group and benzoyl group.

14. A compound represented by Chemical Formula 9:

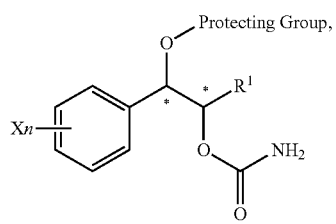

(Chemical Formula 9)

wherein X is one or more independently selected from halogens, n is an integer from 1 to 5, and $R^1$ is selected from the group consisting of a linear or branched alkyl group having 1-10 carbon atoms.

15. The compound according to claim 10, wherein the protecting group is selected from the group consisting of a trimethyl silyl group (TMS), triisopropyl silyl (TIPS), t-butyl and dimethyl silyl (TBDMS), and t-butyl diphenyl silyl (TBDPS).

16. The compound according to claim 12 or claim 13, wherein the protecting group is selected from the group consisting of a trimethyl silyl group (TMS), triethyl silyl group (TES), triisopropyl silyl (TIPS), mothoxymethyl ether (MOM), 2-methoxyethoxymethyl ether (MEM), and benzoyl group.

17. The compound according to claim 14, wherein the protecting group is selected from the group consisting of a trimethyl silyl group (TMS), triethyl silyl group (TES), triisopropyl silyl (TIPS), an acetyl group, and a benzoyl group.

* * * * *